United States Patent
Oyama et al.

(10) Patent No.: US 6,464,696 B1
(45) Date of Patent: Oct. 15, 2002

(54) ELECTRICAL SURGICAL OPERATING APPARATUS

(75) Inventors: Masahide Oyama, Hino; Kenji Harano, Hachioji; Hiroyuki Takahashi, Akishima; Kazuya Hijii, Hachioji, all of (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 09/512,778

(22) Filed: Feb. 24, 2000

(30) Foreign Application Priority Data

| Feb. 26, 1999 | (JP) | 11-051570 |
| Mar. 5, 1999 | (JP) | 11-059272 |
| Mar. 8, 1999 | (JP) | 11-060677 |

(51) Int. Cl.$^7$ .............................. A61B 18/04
(52) U.S. Cl. .............................. 606/34; 606/37; 606/38
(58) Field of Search .................. 606/32–35, 37–40

(56) References Cited

U.S. PATENT DOCUMENTS

| 4,102,341 | A | * | 7/1978 | Ikuno et al. ............... 606/35 |
| 4,416,277 | A | * | 11/1983 | Newton et al. ............ 128/908 |
| 4,590,934 | A | * | 5/1986 | Malis et al. ................ 606/37 |
| 4,969,885 | A | * | 11/1990 | Farin ......................... 128/908 |
| 5,234,427 | A | * | 8/1993 | Ohtomo et al. ............ 606/37 |
| 5,312,401 | A | * | 5/1994 | Newton et al. ............ 606/35 |
| 5,370,645 | A | * | 12/1994 | Klicek et al. .............. 606/34 |
| 5,720,744 | A | * | 2/1998 | Eggleston et al. ......... 606/38 |
| 5,836,943 | A | * | 11/1998 | Miller, III ................. 606/34 |
| 5,931,836 | A | * | 8/1999 | Hatta et al. ................ 606/34 |

FOREIGN PATENT DOCUMENTS

| JP | 4-30509 | 3/1994 |
| JP | 8-5687 | 2/1996 |
| JP | 2545058 | 7/1996 |

\* cited by examiner

*Primary Examiner*—Linda C. M. Dvorak
*Assistant Examiner*—Kenneth G Schopper
(74) *Attorney, Agent, or Firm*—Ostrolenk, Faber, Gerb & Soffen, LLP

(57) ABSTRACT

An electric surgical operation apparatus comprises: an active electrode which performs medical treatment to an area to be treated by applying electric energy to the area; an electric power supplying unit which supplies electric power to the active electrode; a measuring unit which measures at least one of the electrical power output voltage value supplied to the active electrode from the electric power supplying unit, and the output current value thereof; a discerning unit for discerning whether or not the change in at least one of the voltage value and the current value measured by the measuring unit has attained a predetermined change amount; and a voltage control unit for controlling the electric power supplying unit so that the supplied electric power is a constant voltage, according to the discerning results discerned by the discerning unit.

20 Claims, 29 Drawing Sheets

CONVENTIONAL EXAMPLE

LOOP ELECTRODE

CONVENTIONAL EXAMPLE

BAND ELECTRODE

CONVENTIONAL EXAMPLE

ROLLER ELECTRODE

CONVENTIONAL EXAMPLE

CONVENTIONAL EXAMPLE

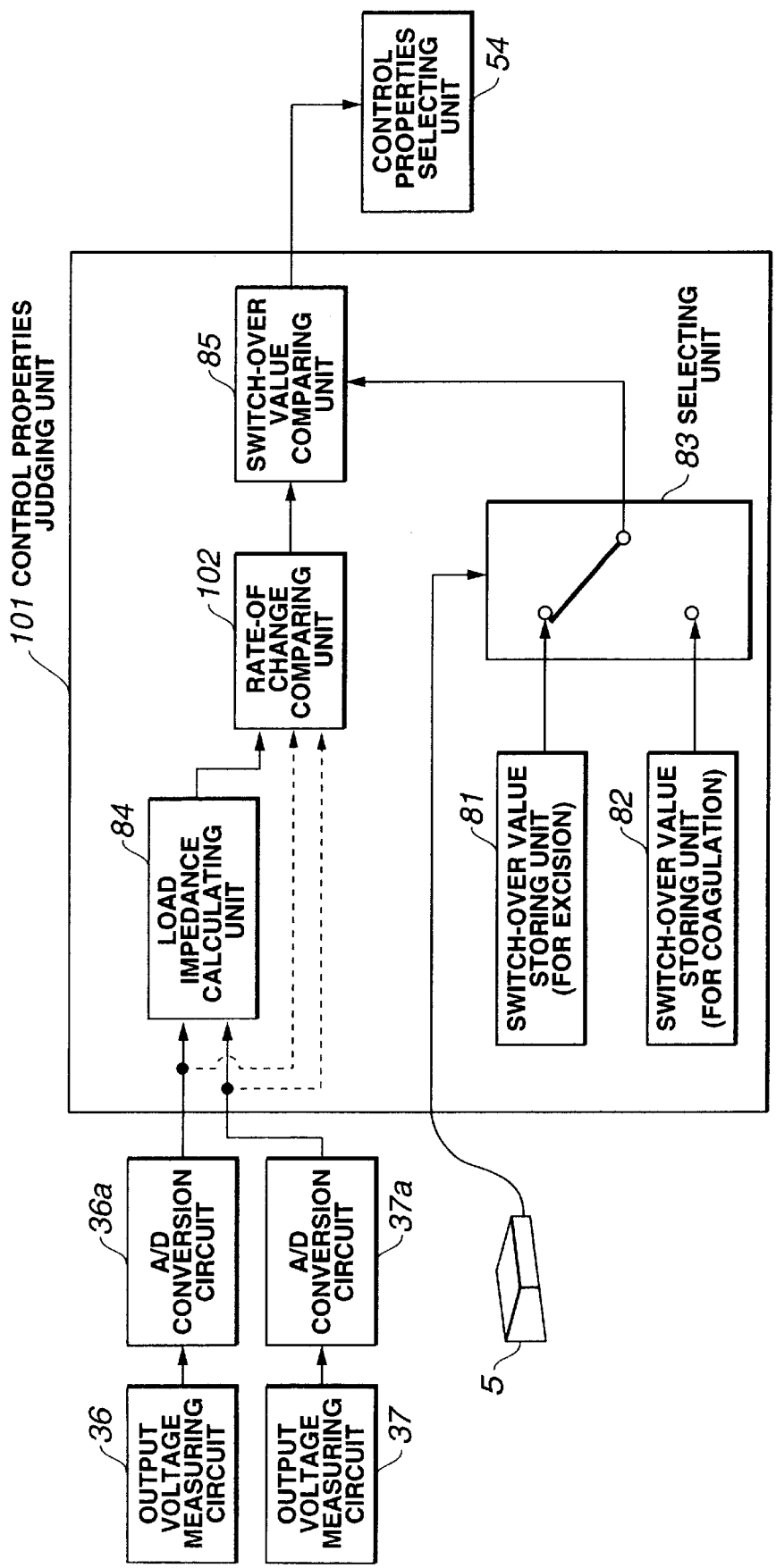

ELECTRICAL SURGICAL OPERATING APPARATUS

BACKGROUND OF THE INVENTION

1. Field of the Invention

The present invention relates to an electric surgical operating apparatus which performs medical treatment to organism tissue and the like such as excision and coagulation, using high-frequency electric power.

2. Description of the Related Art

In recent years, electric surgical operating apparatuses which perform medical treatment to organism tissue and the like such as excision and coagulation by using high-frequency electric power have come to be known. Generally, such electric surgical operating apparatuses are configured having a high-frequency cauterization electric power source device for generating high-frequency electric current, and a high-frequency cauterization treating instrument provided with an active electrode for coming into contact with the area of the patient to be treated, and executing medical treatment with high-frequency electric current.

Regarding the types of the high-frequency cauterization treating instrument, monopolar treating instruments and bipolar treating instrument are known.

Monopolar treating instruments are configured having an active electrode which is connected to one output terminal of the high-frequency cauterization electric power source device and comes into contact with the area of the patient to be treated, and a feedback terminal portion which is connected to the other output terminal and is in plan contact with the body surface of the patient at a portion other than the area of the patient to be treated. The high-frequency cauterization electric power source device generates high-frequency electric power, this high-frequency electric power is concentratedly introduced into the organism tissue via the active electrode which is in contact with the area to be treated, and this high-frequency electric current is dispersed and recovered by the feedback electrode, thus enabling medical treatment to be performed on the organism tissue, such as excision, coagulation, and the like.

Conversely, bipolar treating instruments do not have a feedback electrode, with the line portion from which the active electrode extends being connected to both output terminals of the high-frequency cauterization electric power source device. There are various forms of the active electrode, according to use. For example, the is a loop-shaped loop electrode such as shown in FIG. 1A, a band-shaped band electrode such as shown in FIG. 1B, a roller-shaped roller electrode such as shown in FIG. 1C, and so forth.

Generally, once the supply of high-frequency electric power from the high-frequency cauterization electric power source device to the active electrode begins, heat is transferred to the organism tissue from the active electrode which has generated heat due to this high-frequency electric power. This generated heat causes transpiration of the organism tissue resulting in tissue degeneration, and as shown in FIG. 2, load impedance increases with time. Then, voltage drop owing to load impedance increases, and the output voltage of the electric surgical operation apparatus increases. When the output voltage reaches the predetermined voltage VE, arc discharge from the active electrode to the organism tissue is started. This arc discharge starts the excision operation on the organism tissue.

Incidentally, the reference symbols a, b, and c in FIG. 2 indicate that the properties of the active electrodes differ according to the electrode form, size, volume, material, and so forth. Also, in addition to the excision operation performed on the organism tissue, a coagulation operation can be performed, by modulating the waveform of the high-frequency current into a intermittent waveform, or lowering the output voltage in comparison with the voltage at the time of excision, thus facilitating hemostasis.

The output power of such an electric surgical operating apparatus exhibits properties such as shown in FIG. 3 as to the load impedance which is the impedance of the organism tissue.

That is, in the event that the load impedance is within a predetermined range from the rated load impedance, the rated output electric power necessary for performing the treatment to the area to be treated can be obtained, but in the event that the load impedance is smaller or greater than this range, the output voltage decreases, and output electric power necessary for performing the treatment to the area to be treated cannot be obtained.

Incidentally, the organism tissue prior to supply of high-frequency electric power to the active electrode normally contains a great deal of moisture, so the load impedance is small, and the rated output power cannot be obtained.

Also, the output power reaches the maximum value when the load impedance is near the predetermined rated load impedance value. The farther the load impedance value is from the rated load impedance, the smaller the output power is. Thus, the load impedance changes according to the state of the above-described tissue deterioration, consequently allowing the output power to change, so optimal output voltage for performing excision or coagulation cannot be obtained.

For example, in the event that the output voltage at the time of performing the excision operation is great, high-density discharge energy is transferred to the organism tissue when conducting the arc discharge. Conversely, in the event that the output voltage is small, there is no arc discharge. Consequently, trouble similar to that in excision occurs for performing coagulation as well, in the event that optimal output voltage for coagulation cannot be obtained. This means that the speed and so forth of tissue deterioration differs from that which the operator intends, due to optimal output voltage not being obtained.

Accordingly, means are provided in the First Embodiment of the high-frequency electric scalpel apparatus disclosed in Japanese Unexamined Utility Model Publication 4-30509 measures the output voltage value so that the stability of excision and coagulation operations can be improved by setting an appropriate target value, thereby comparing the output voltage value with the set target value and increasing or reducing the gain of the output circuit to maintain the output voltage value at the target value by performing constant-voltage control, whereby change in the output voltage is reduced as to change in the load impedance. Also, means for performing constant-voltage control and constant-power control are described in another embodiment disclosed in this Japanese Unexamined Utility Model Publication 4-30509, but these cannot be applied to the object of stabilizing the output voltage.

Also, with the electric surgical operation apparatus such as shown in FIG. 2, there is the problem of a delay in time occurring from the point of starting output of the electric power to the time of starting the excision or coagulation operation to the area to be treated. Also, increasing the output current in order to accelerate the deterioration of the organism tissue speeds up the increase of load impedance, but there has been a problem in that excessive power is output even after the load impedance reaches the necessary value.

Accordingly, the high-frequency electric scalpel apparatus in Japanese Patent No. 2542058 for example discloses means which enables control to be made such that the output current increases for a predetermined amount of time following starting of power output, wherein power with increased current is output during the period immediately following starting power output when the load impedance is small so as to accelerate tissue deterioration, following which appropriate power output can be made after a certain amount of time. This shortens the amount of delay in time from starting power output to the start of the excision/coagulation operation.

Further, the treating instrument of the above-described electric surgery operating apparatus is generally provided with an insulating covering at places other than the electrode. However, in the event that this insulating covering is damaged and insulation destruction occurs, this can cause trouble such as the insulation destruction portion coming into contact with the organism tissue causing the organism tissue to heat and deteriorate, decrease in voltage applied to the area to be treated, and so forth. Accordingly, with electric surgery operating apparatus, attention is paid to the voltage withstanding properties of the treating instrument when using.

The main unit of the electric surgery operating apparatus generally allows the output power level thereof to be adjusted, and the output voltage changes according to the setting state of this output power level. Thus conventionally, the output power level is adjusted while the technician takes care that the output voltage value does not exceed the maximum usage voltage value of the treating instrument, based on the maximum usage voltage value information provided in the operating manual of the treating instrument, and information of properties of the output voltage corresponding to the state of setting the output power levels as described in the operating manual of the electric surgery operating apparatus, which has been troublesome to the extent of being a problem.

In order to solve this problem, Japanese Examined Utility Model No. 8-5687 describes a means wherein, with a high-frequency electric scalpel apparatus arranged such that a special treating instrument having the function of telling the electric surgery operation apparatus the voltage withstanding value being connected to the main unit of the electric surgery operation apparatus, the maximum voltage value of high-frequency electric power which can be applied to the connected treating instrument is automatically recognized, and control is made so that the output voltage from the electric surgery operation apparatus does not exceed the maximum voltage value.

However, with generally-used electric surgery operation apparatuses, the output power can be adjusted, and such apparatuses are arranged such that the speed and the like of tissue deterioration can be adjusted by changing the output power. However, according to the means of the First Embodiment described in the aforementioned Japanese Unexamined Utility Model Publication No. 4-30509 setting the target value in order to adjust the output power results in the output voltage at the time of performing excision or coagulation changing, so appropriate output voltage cannot be obtained for the excision or coagulation; so the setting must be changed again to a target value during treatment in order to obtain output voltage appropriate for the excision or coagulation operation, meaning that there has been a problem in operability.

Also, in the event that the electrode form, size, volume, or material of the active electrode making up the high-frequency cauterization treating instrument differ as shown in FIGS. 1A through 1C, there is difference in the delay time to the start of the excision/coagulation operation as shown in FIG. 2. That is to say, the sense of operating the active electrode differs depending on the form, size, volume, or material thereof, so there has been the problem in unnaturalness in the operability.

Further, with the high-frequency electric scalpel apparatus in the above-mentioned Japanese Examined Utility Model No. 8-5687, the treating instrument connectable to the main unit of the electric surgery operation apparatus is restricted only to specialized ones having functions for telling the electric surgery operation apparatuses of the maximum voltage value, and thus not only was the range of selection of treating instruments limited, but also resulted in treating instruments being expensive. Moreover, though means are disclosed in the above high-frequency electric scalpel apparatus for preventing insulation destruction of the treating instrument, no means are described for detecting the insulation destruction occurring in the event that insulation destruction of the treating instrument actually does occur.

SUMMARY OF THE INVENTION

Accordingly, it is an object of the present invention to provide an electric surgical operating apparatus which performs medical treatment such as excision and coagulation operations in a stable and unintrusive manner, even in the event that the output electric power settings are changed.

It is another object of the present invention to provide an electric surgical operating apparatus which reduces the difference in delay in the time for starting operation which occurs due to different treating instruments having different electrode forms, sizes, volumes, and materials, thereby doing away with the unnaturalness in operating sense.

It is a further object of the present invention to provide an electric surgical operating apparatus which prevents voltage exceeding the voltage withstanding value of the treating instrument being applied thereto, thereby preventing insulation destruction of the treating instrument, without using special treating instruments.

It yet another object of the present invention to provide an electric surgical operating apparatus wherein occurrence of insulation destruction of the treating instrument or the danger thereof is detected, thereby avoiding or facilitating avoidance of problems occurring due to insulation destruction of the treating instrument.

Concisely, the electric surgical operation apparatus according to the present invention comprises:
  an active electrode for performing medial treatment to an area to be treated by applying electric energy to the area;
  an electric power supplying unit which supplies electric power to the active electrode;
  a measuring unit which measures at least one of the electrical power output voltage value supplied to the active electrode from the electric power supplying unit, and the output current value thereof;
  a discerning unit for discerning whether or not the change in at least one of the voltage value and the current value measured by the measuring unit has attained a predetermined change amount; and a voltage control unit for controlling the electric power supplying unit so that the supplied electric power is a constant voltage, according to the discerning results discerned by the discerning unit.

BRIEF DESCRIPTION OF THE DRAWINGS

FIGS. 1 through 3 are diagrams describing conventional examples;

FIG. 1 is an explanatory diagram illustrating forms of electrodes, wherein

FIG. 2 is an explanatory diagram illustrating changes in the properties of load impedance and output voltage over time;

FIG. 3 is an explanatory diagram illustrating the properties of output electric power as to load impedance;

FIG. 4 is an explanatory diagram illustrating the overall configuration of the electric surgical operation apparatus;

FIG. 5 is a diagram describing the configuration of a high-frequency cauterization treating instrument which differs from the high-frequency cauterization treating instrument shown in FIG. 4;

FIG. 6 is a block diagram illustrating the configuration of the high-frequency cauterization electric power source device;

Figure 8:
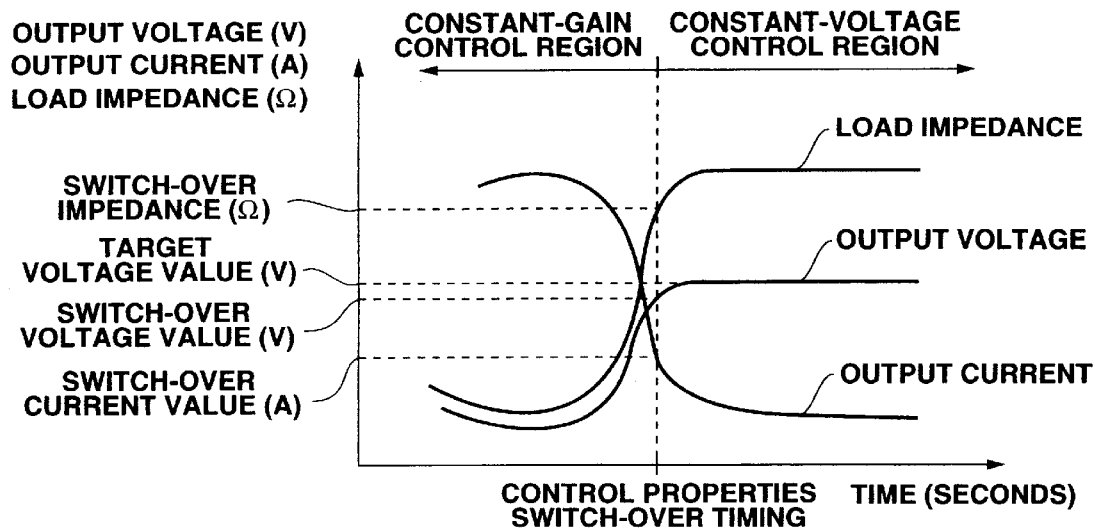
Figure 9:
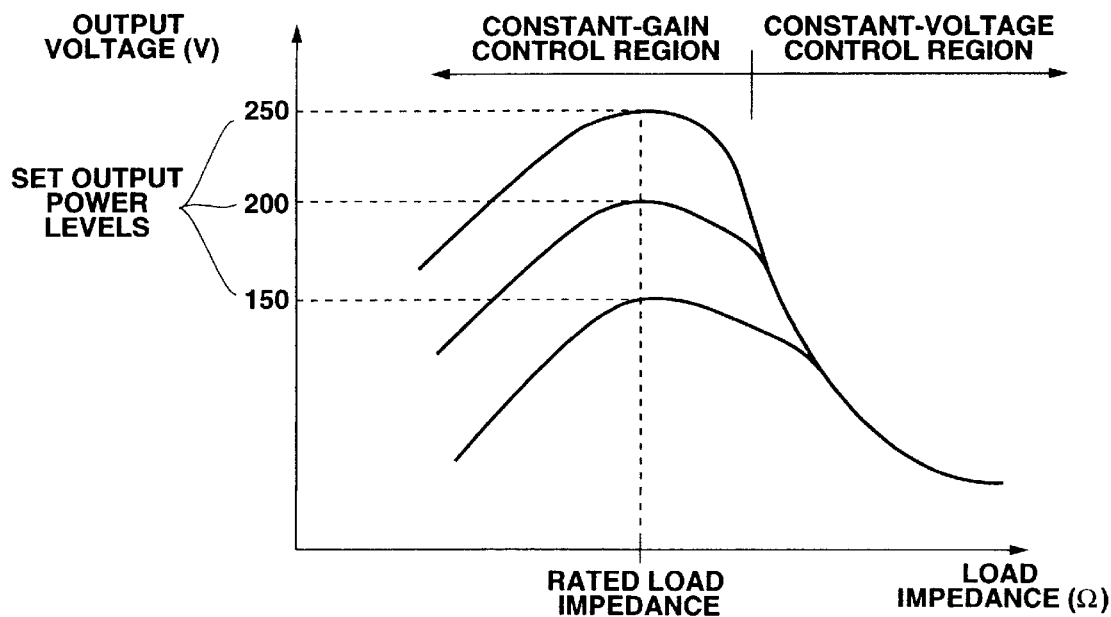
Figure 10:
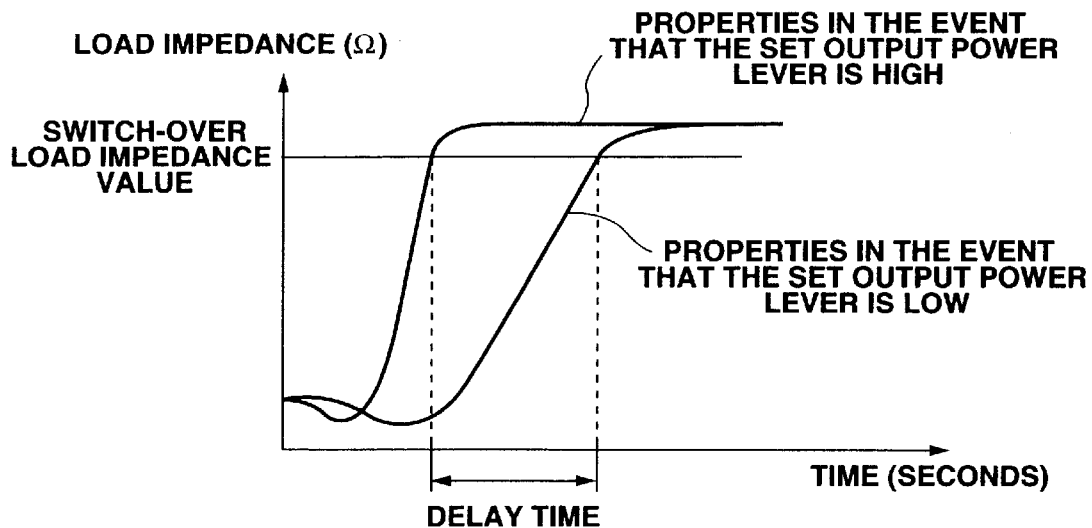
Figure 12:
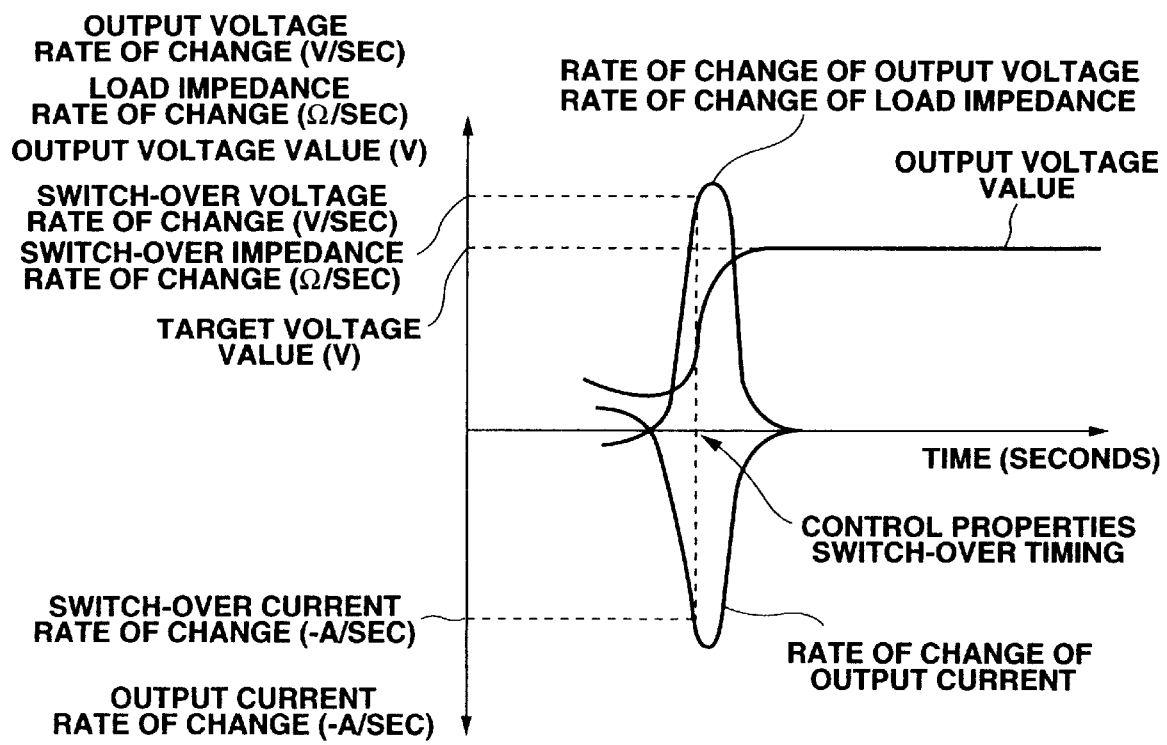
Figure 13:
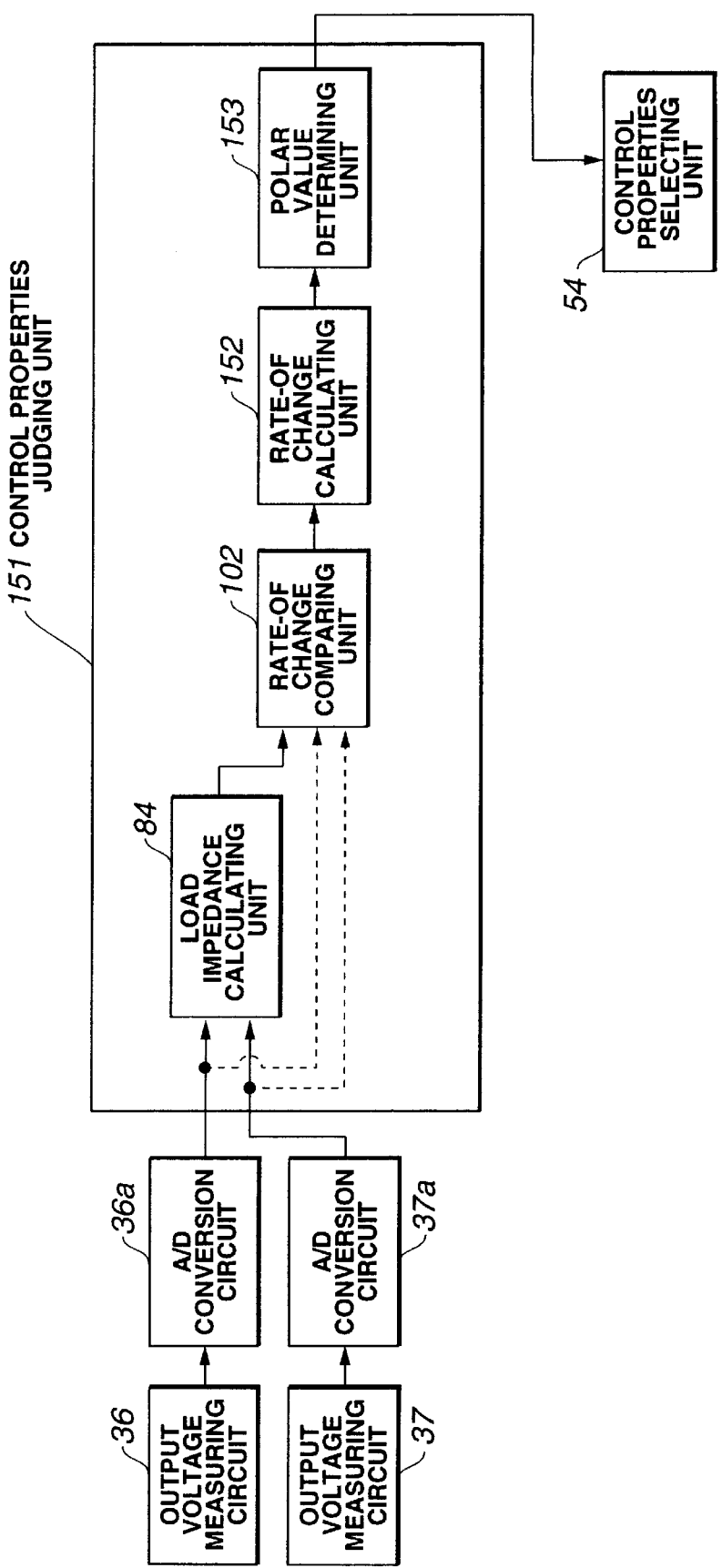
Figure 14:
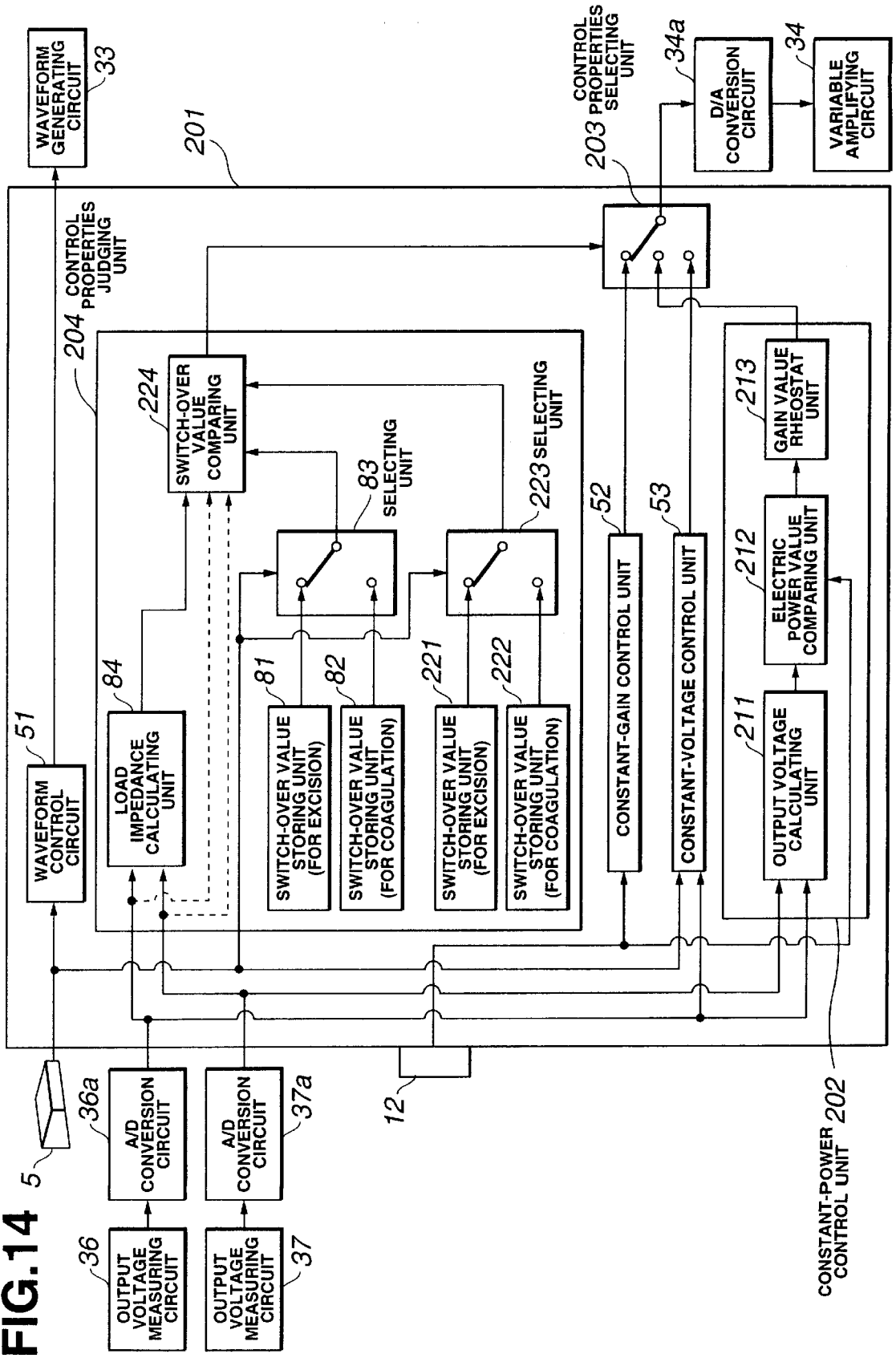
Figure 15:
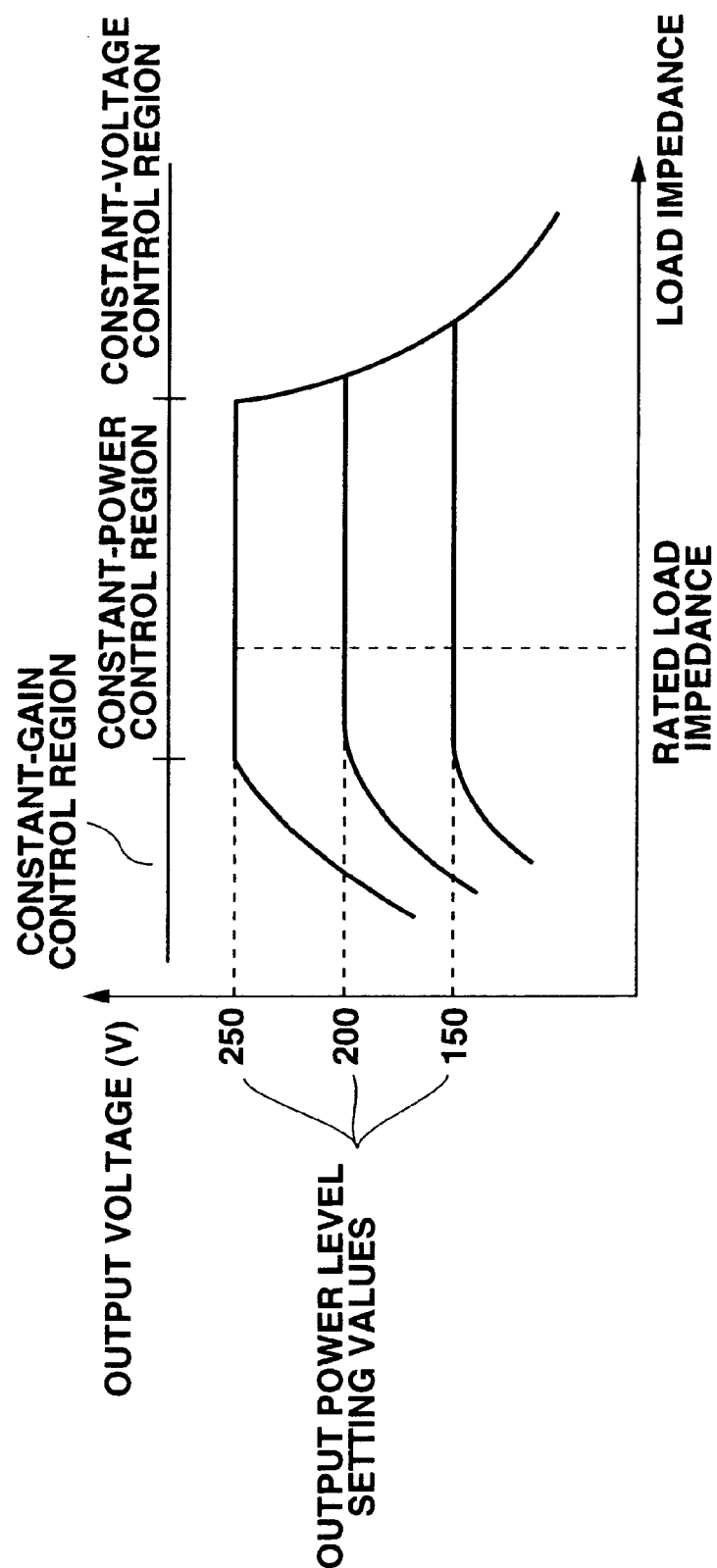
Figure 16:
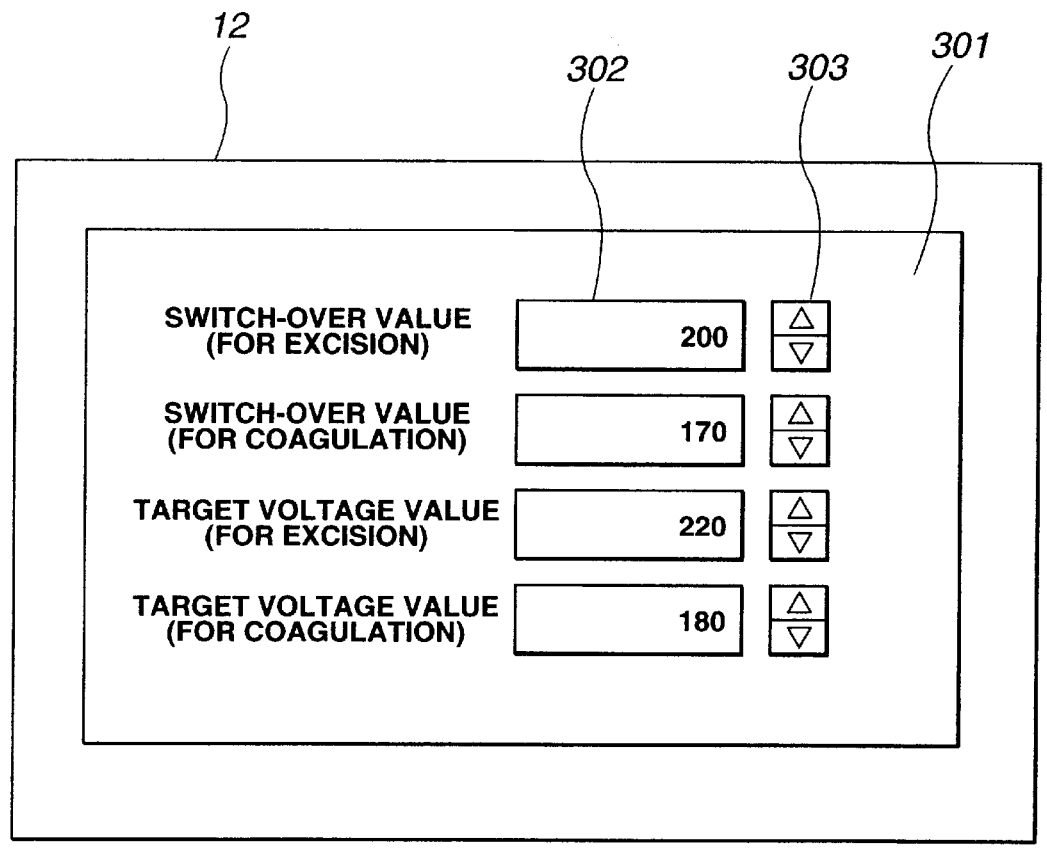
Figure 17:
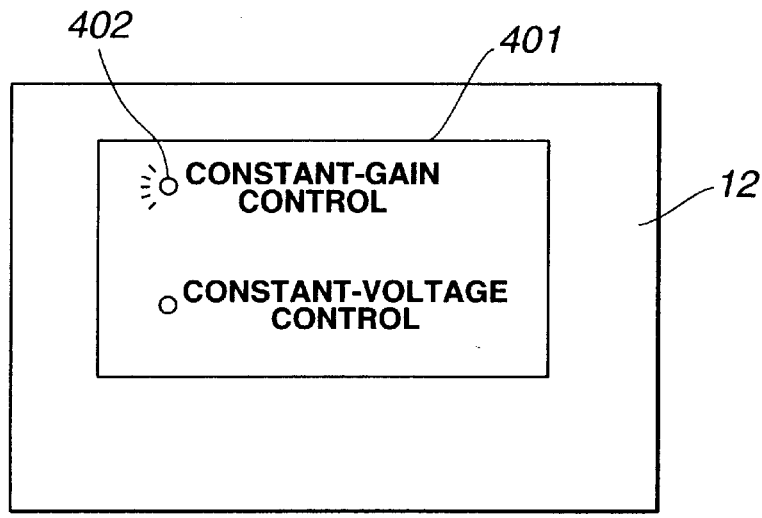
Figure 20:
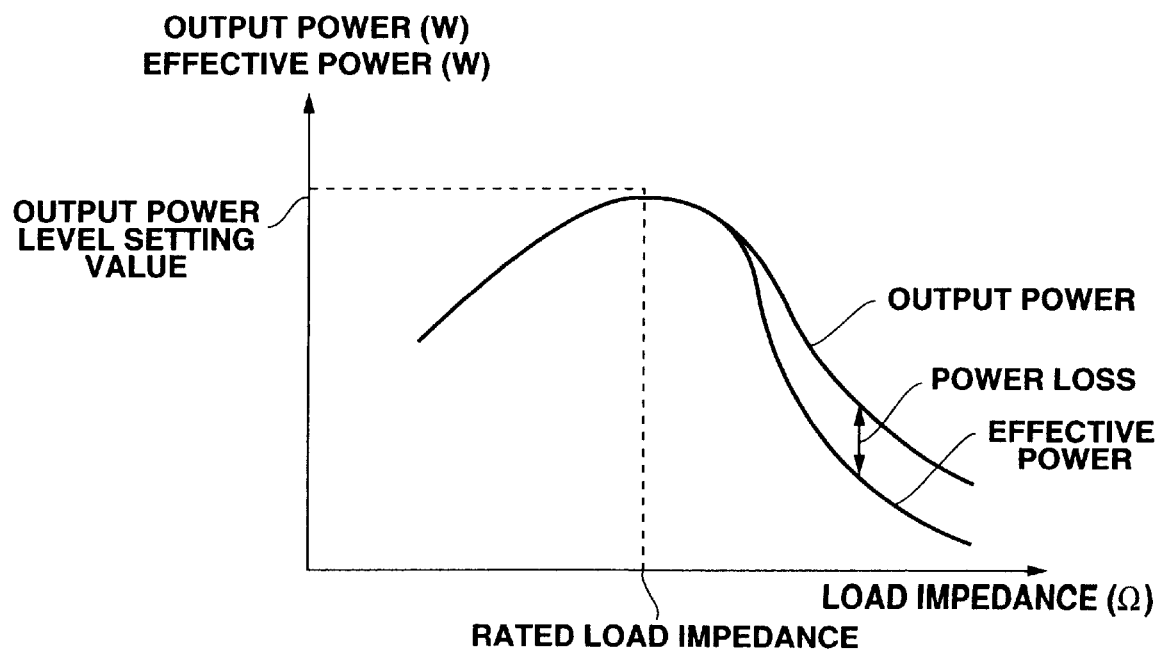
Figure 18:
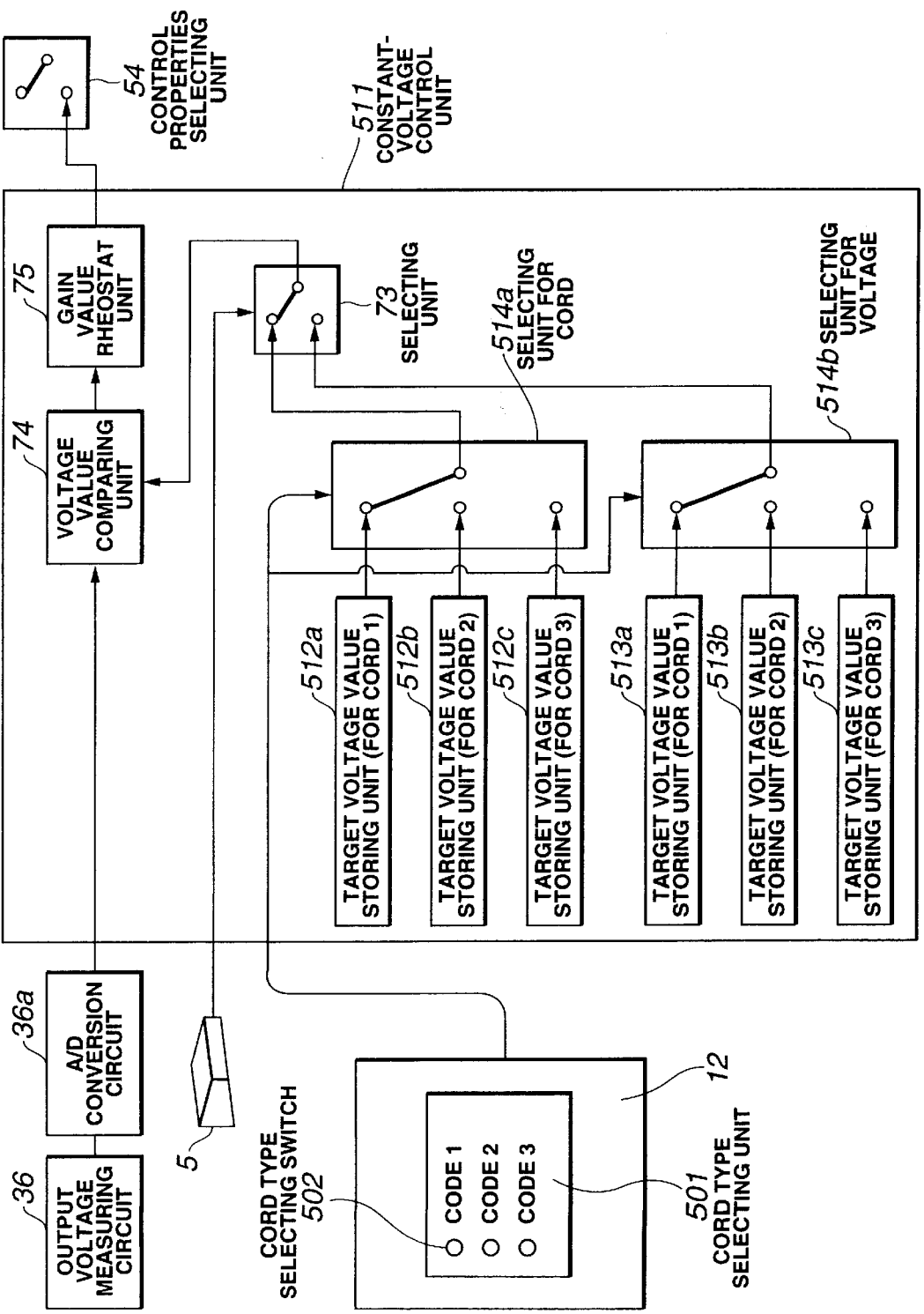
Figure 19:
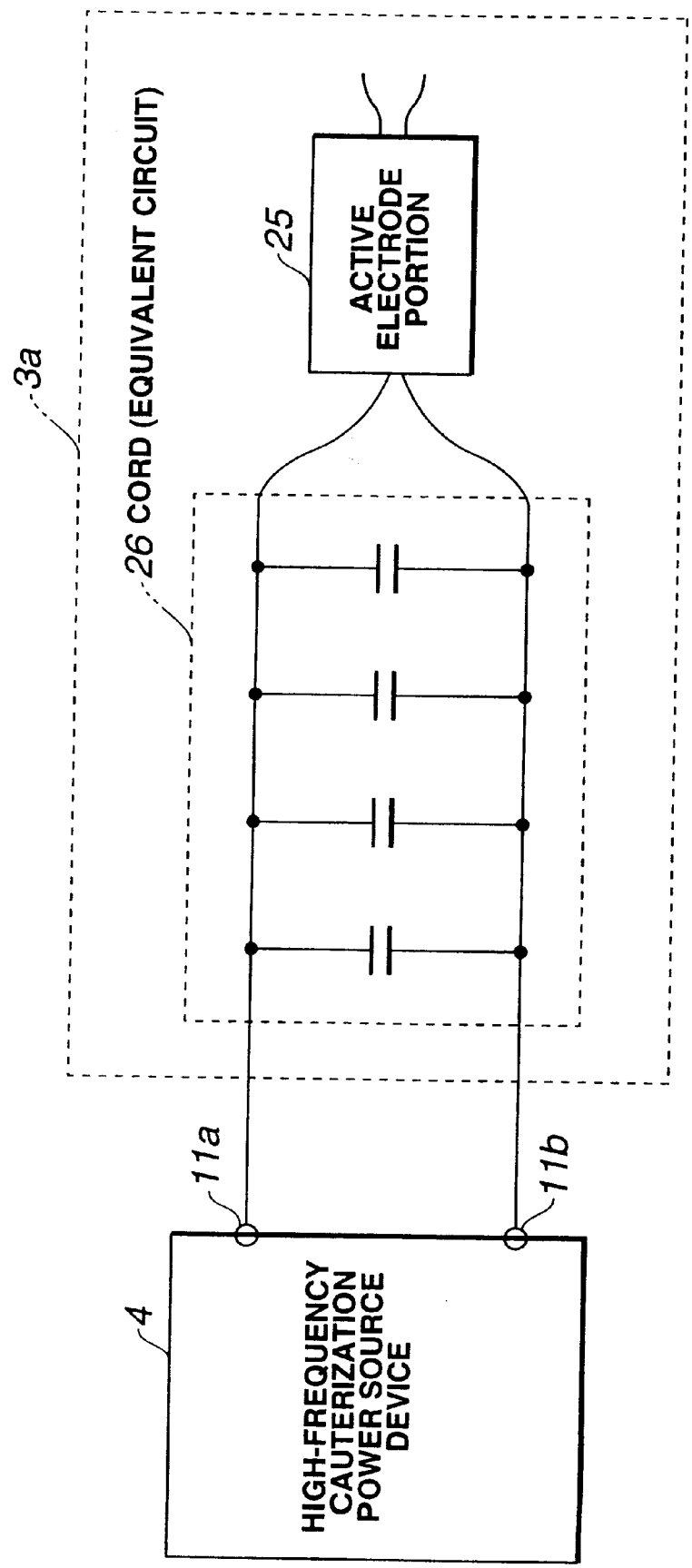
Figure 21:
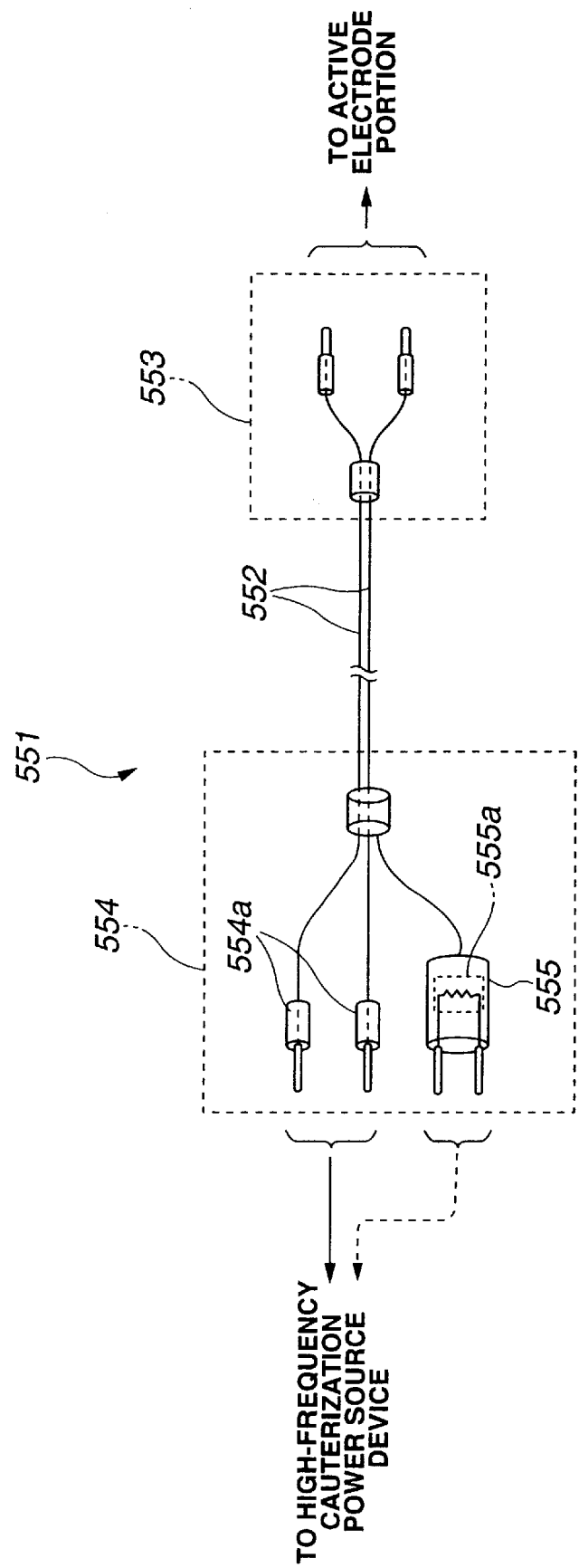
Figure 22:
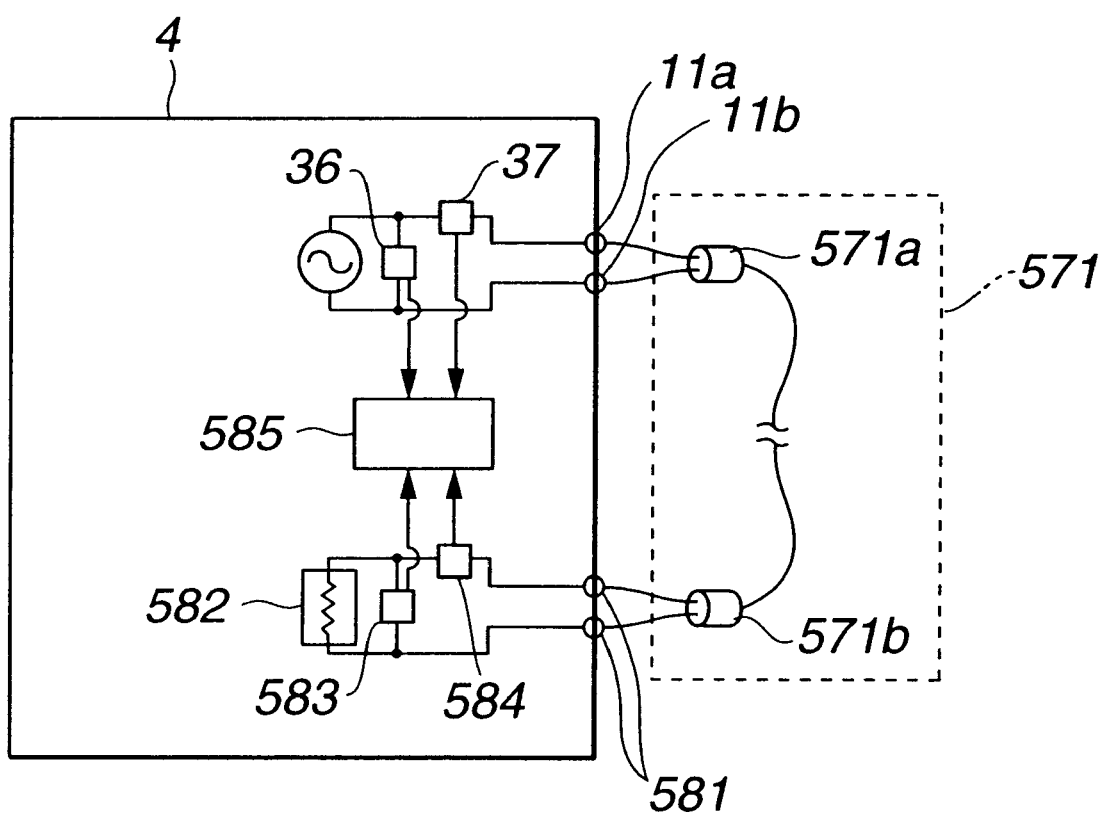
Figure 23:
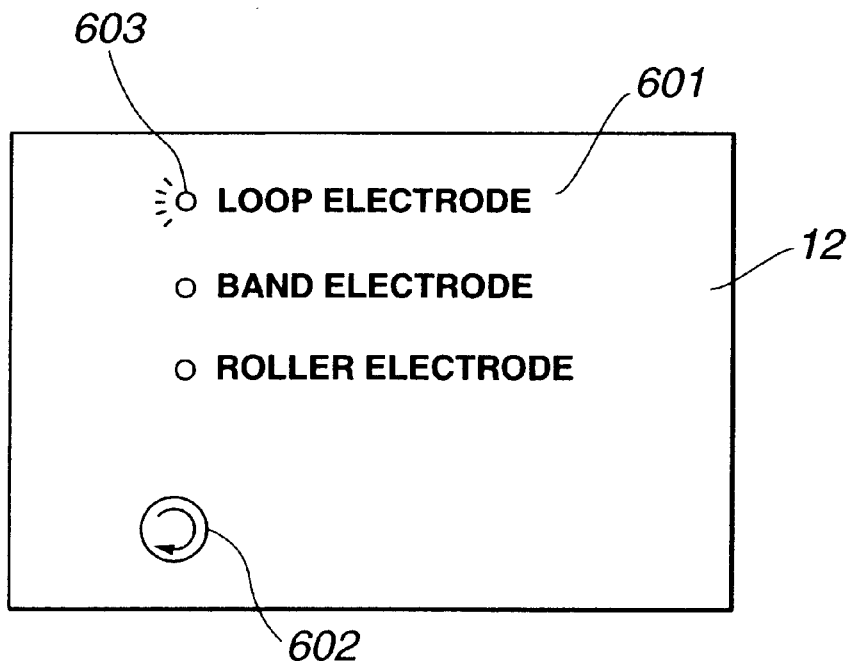
Figure 27:
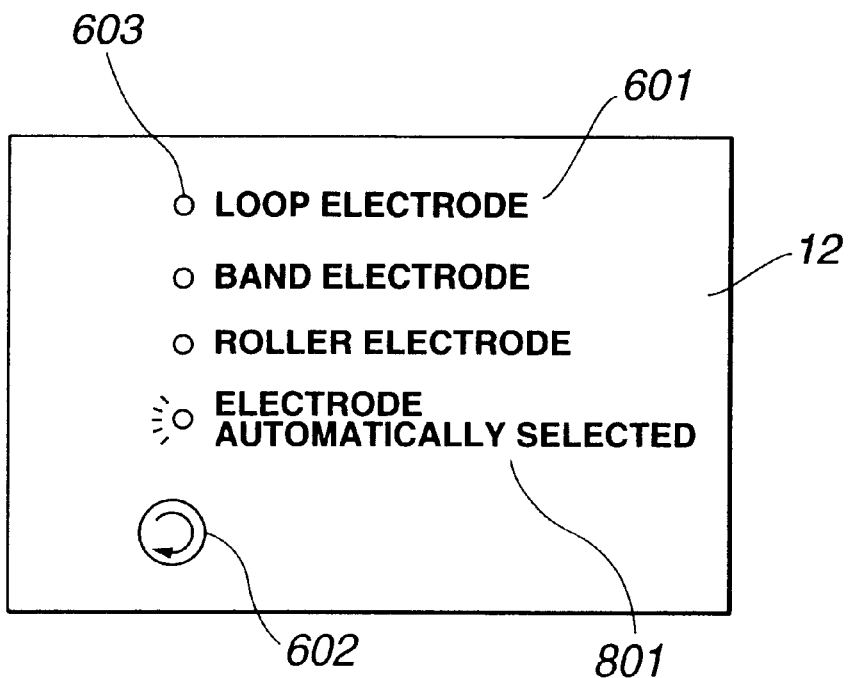
Figure 24:
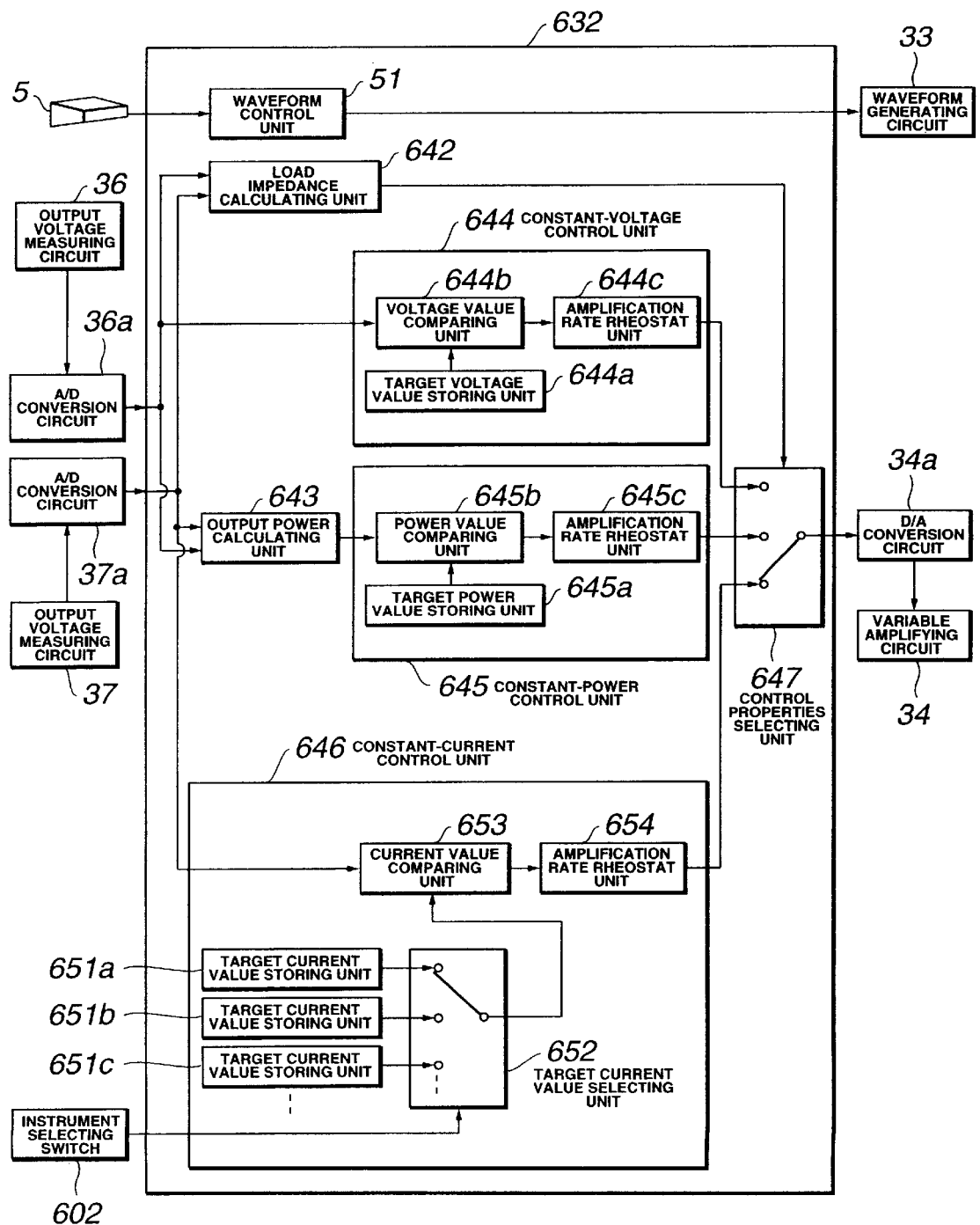
Figure 25:
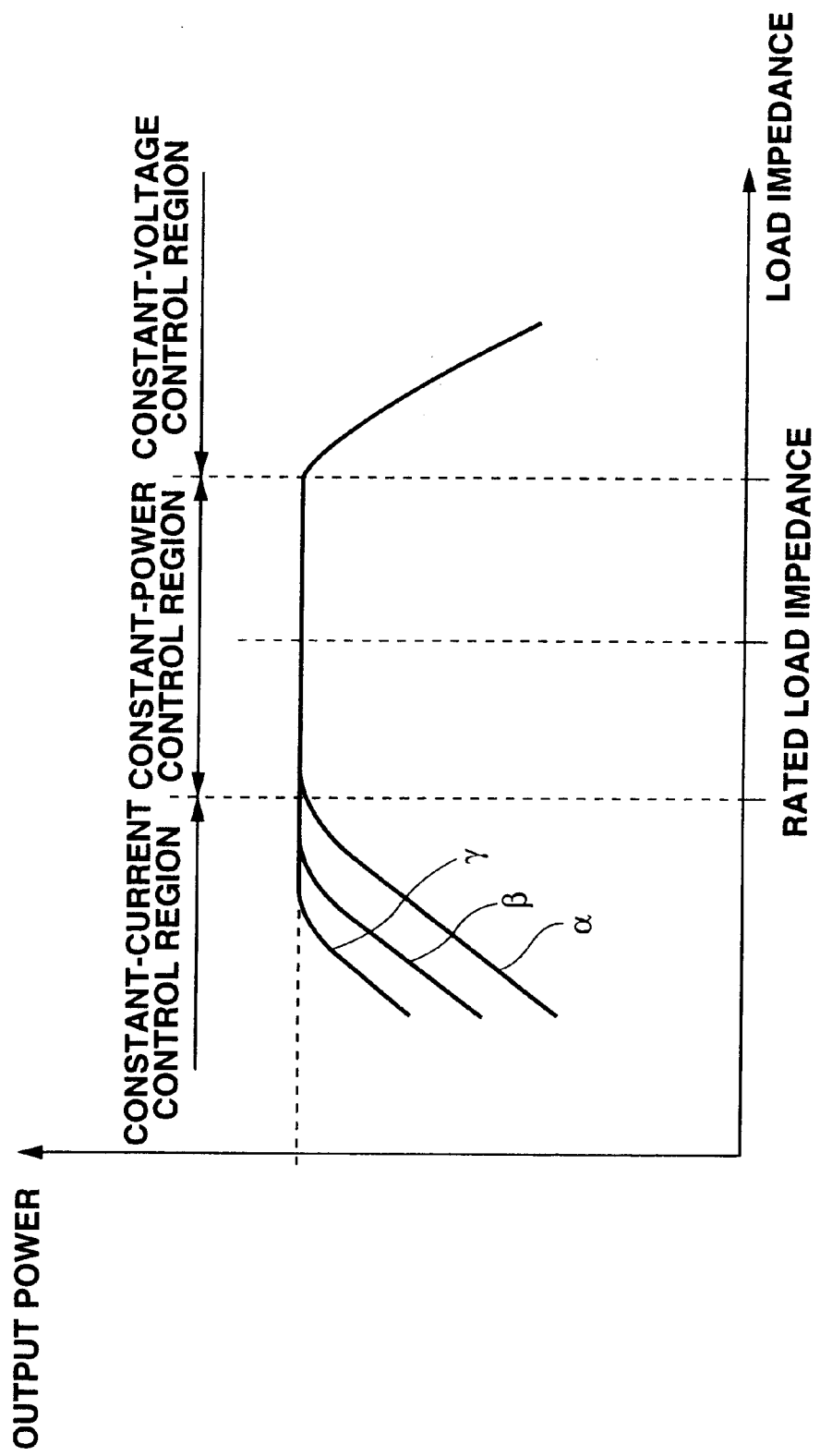
Figure 26:
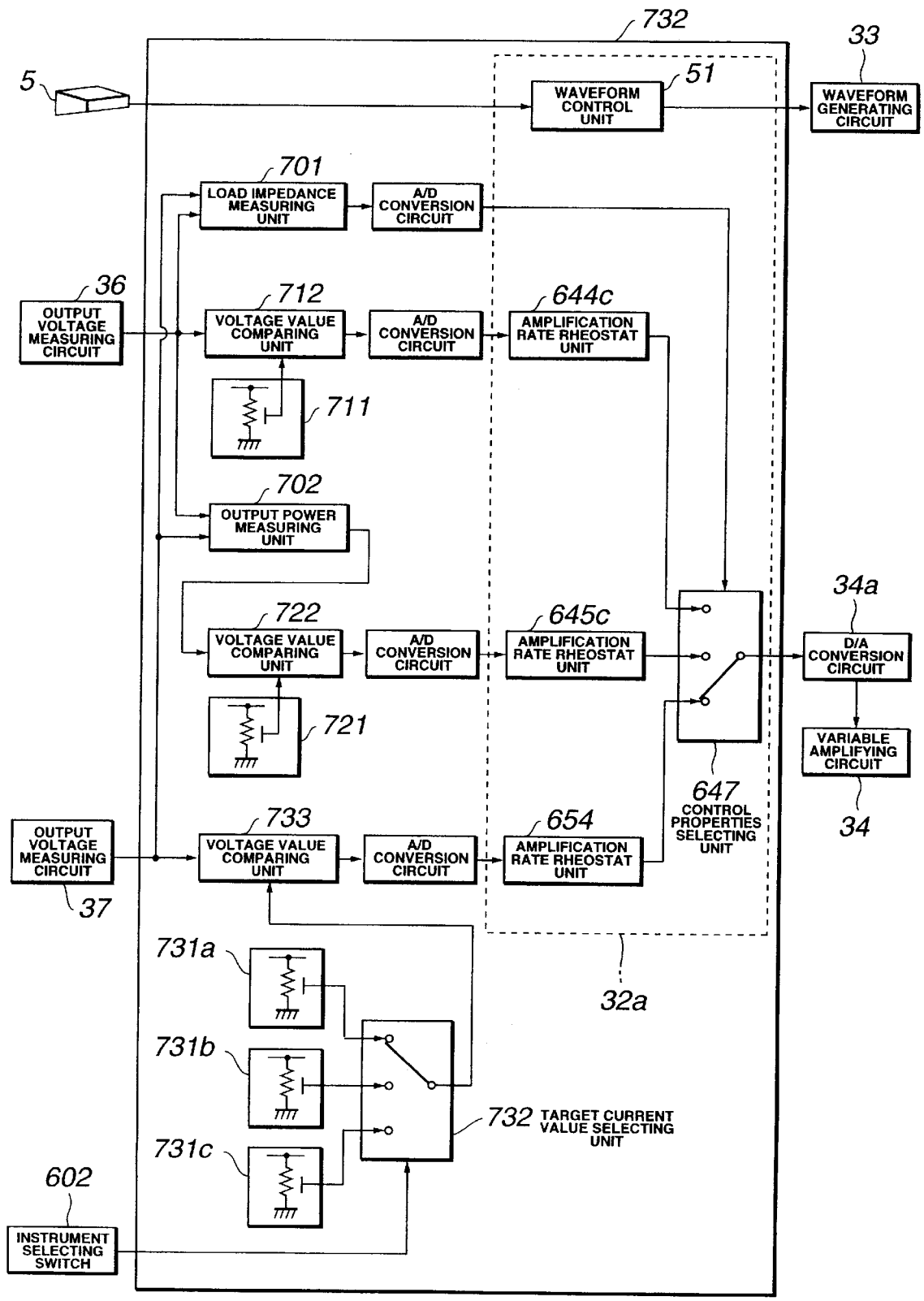
Figure 28:
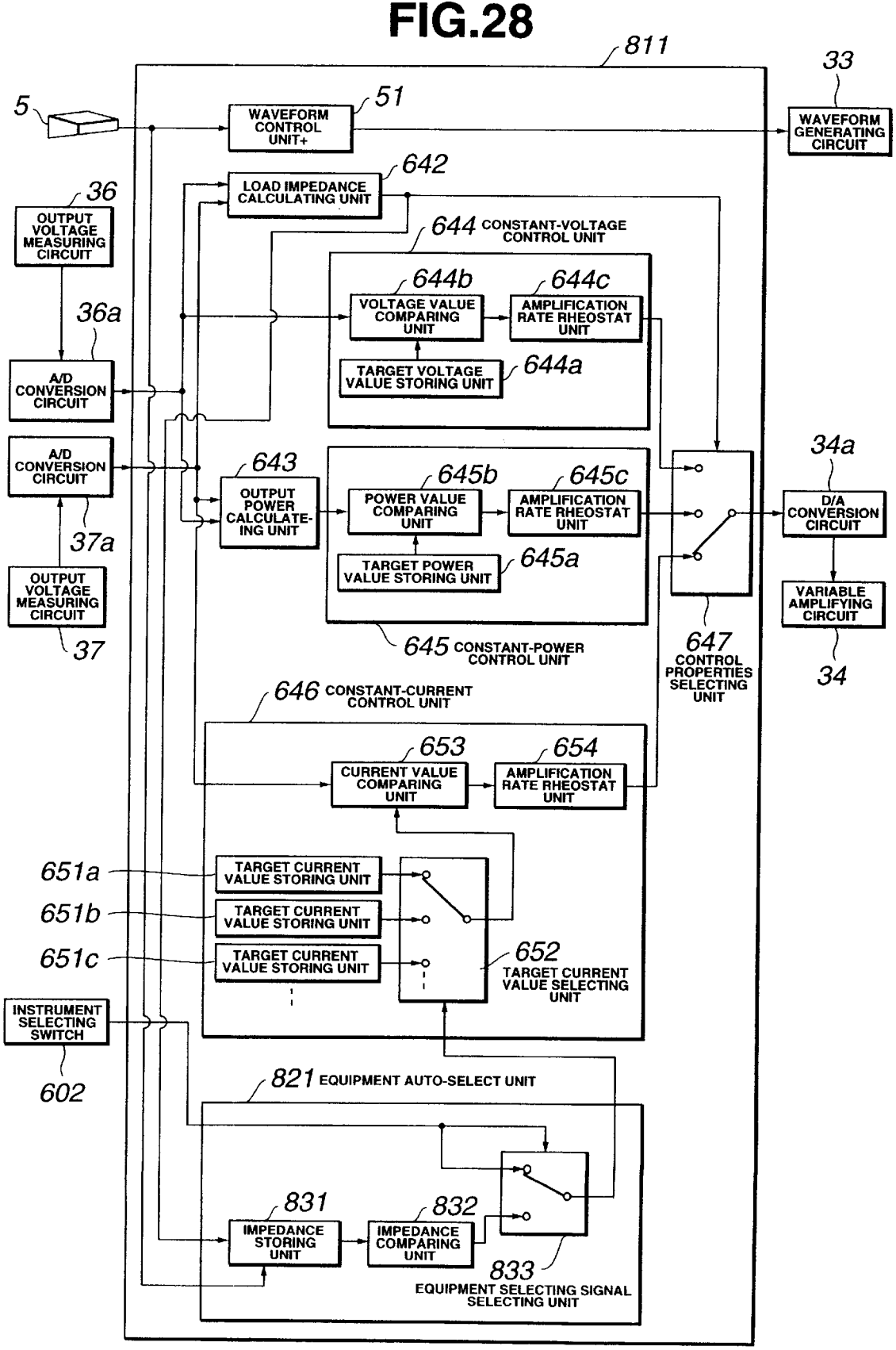
Figure 29:
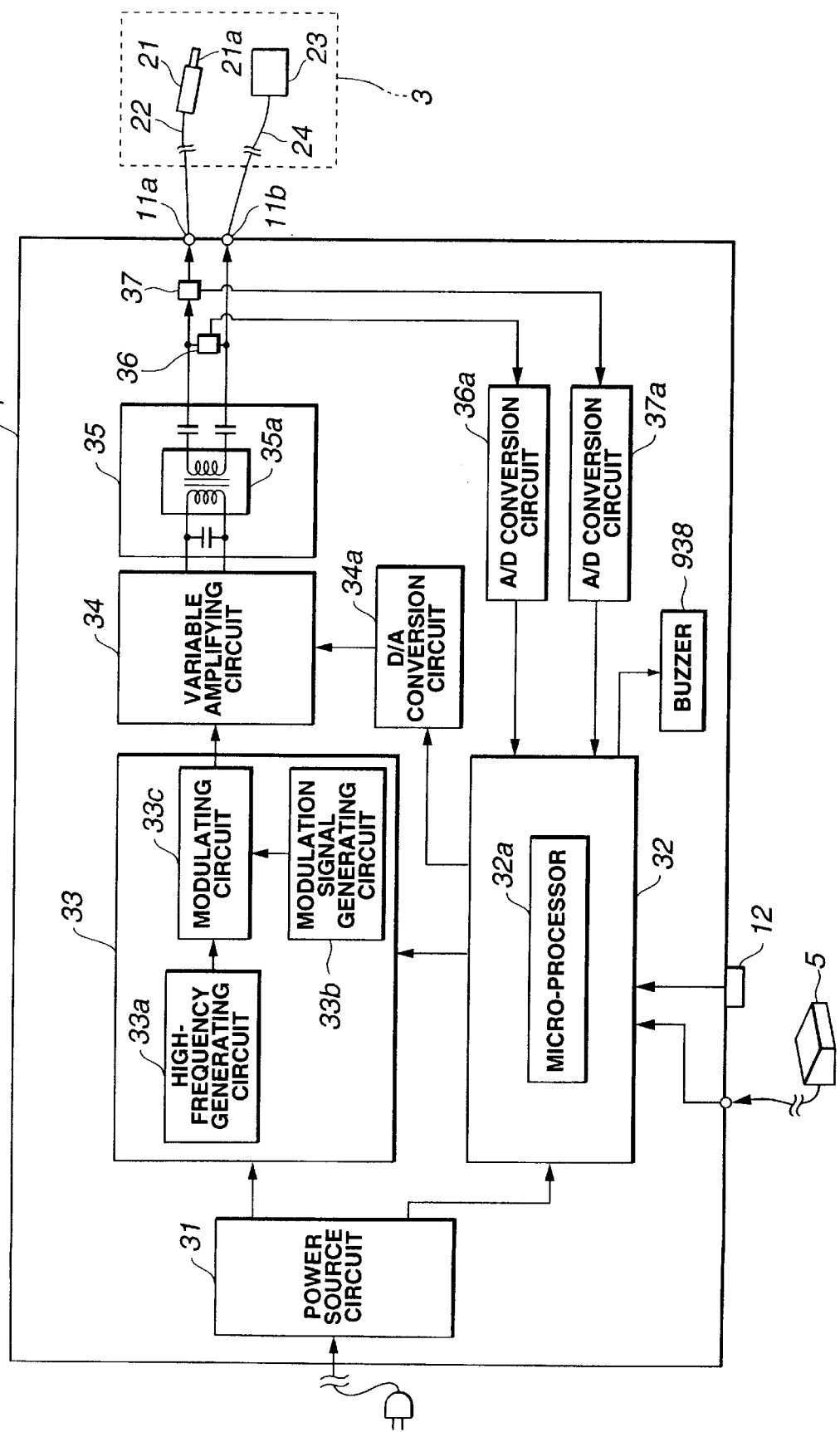
Figure 30:
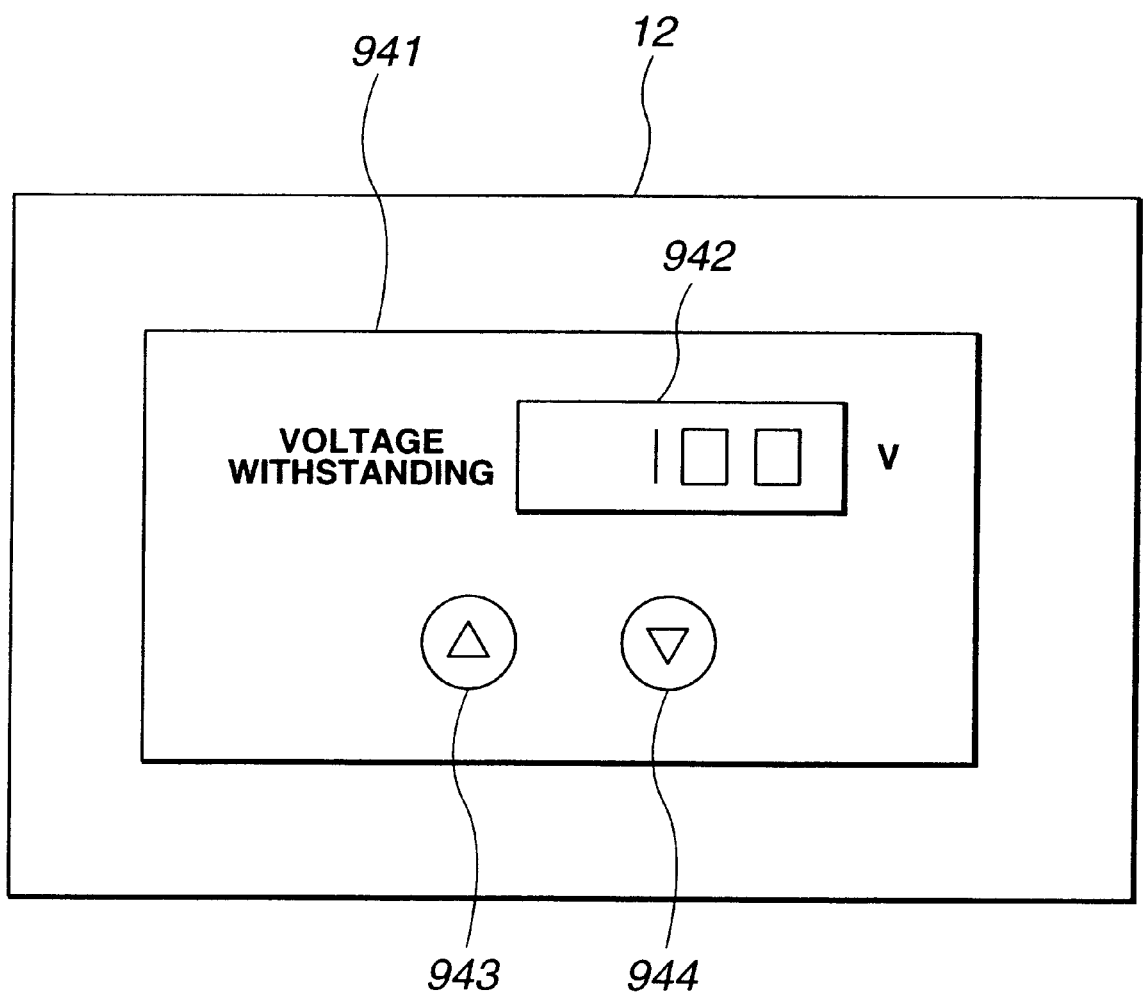
Figure 31:
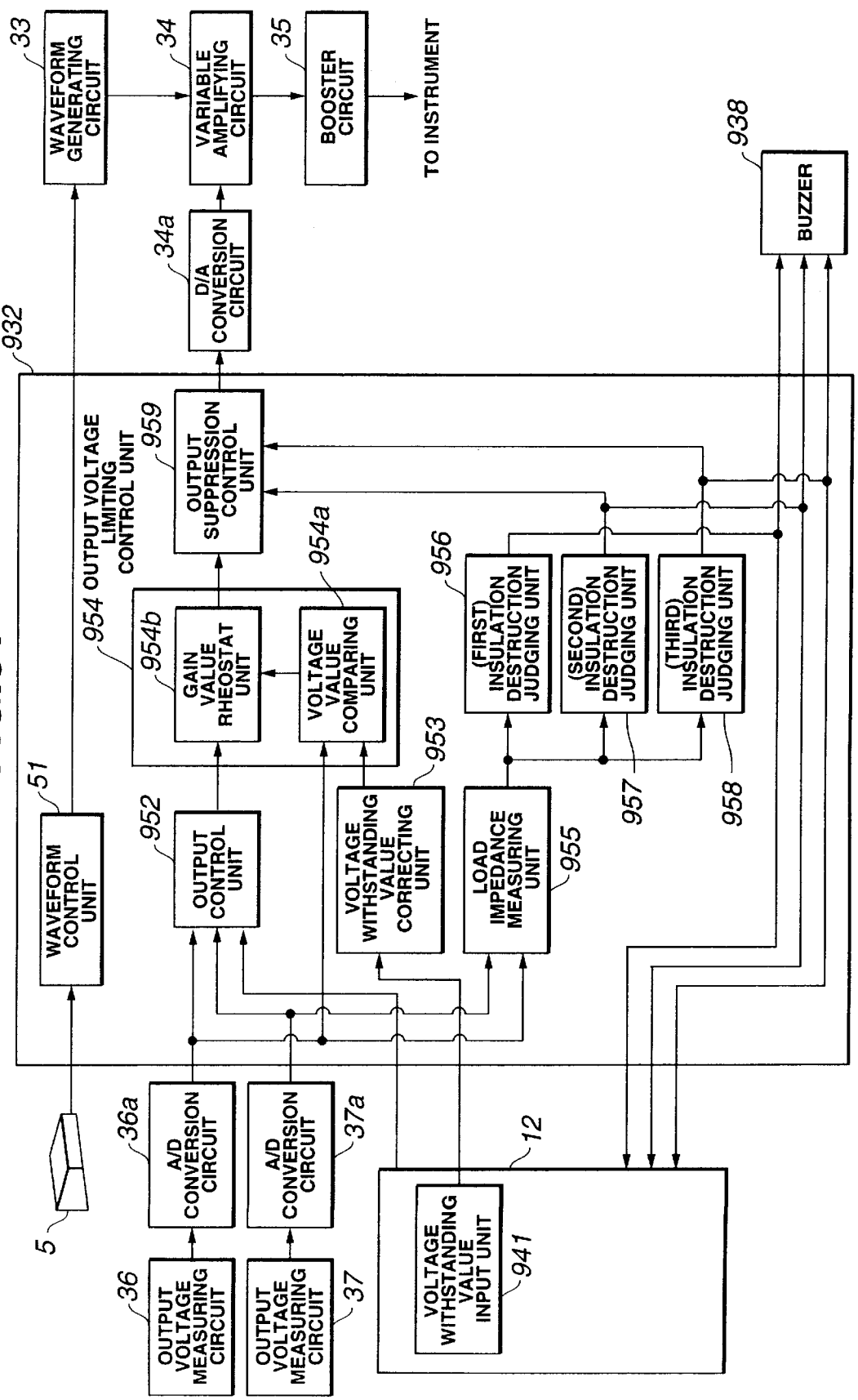
Figure 32:
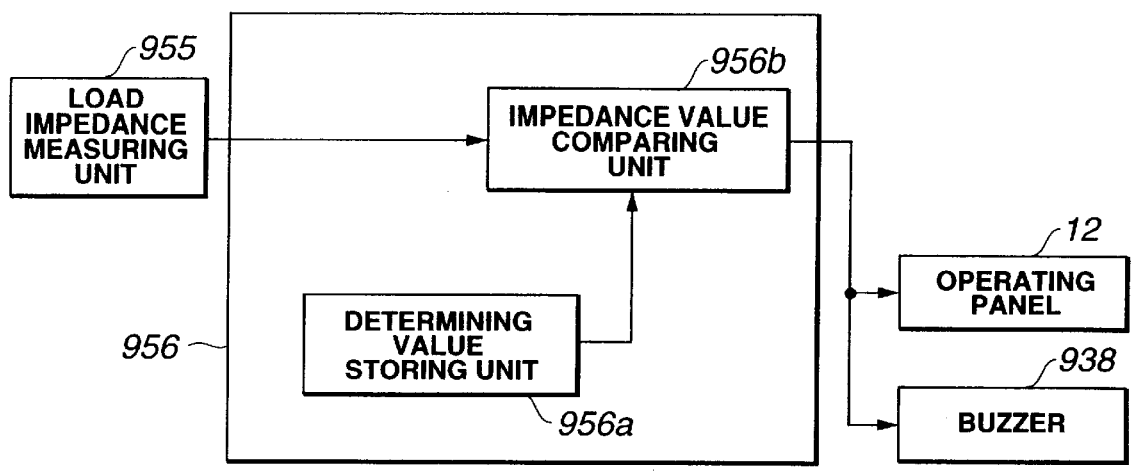
Figure 33:
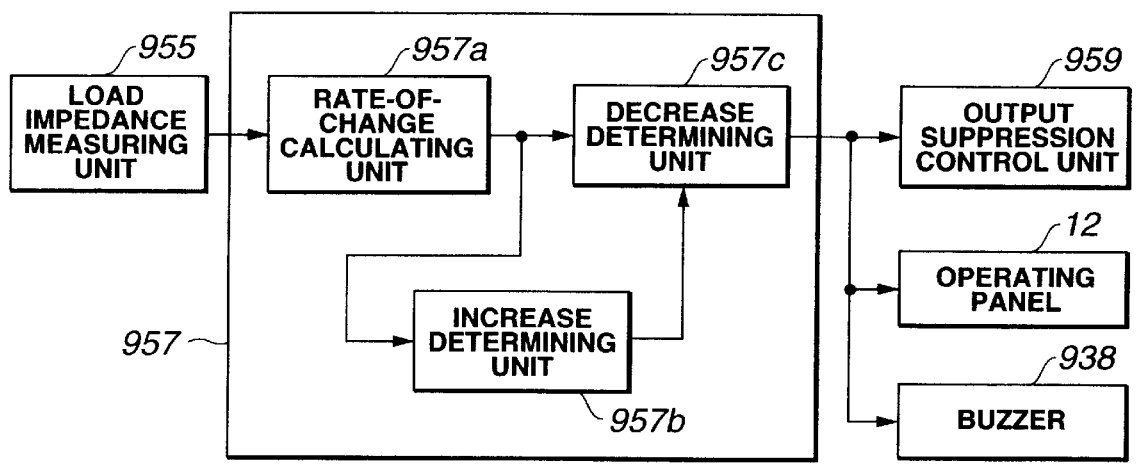
Figure 34:
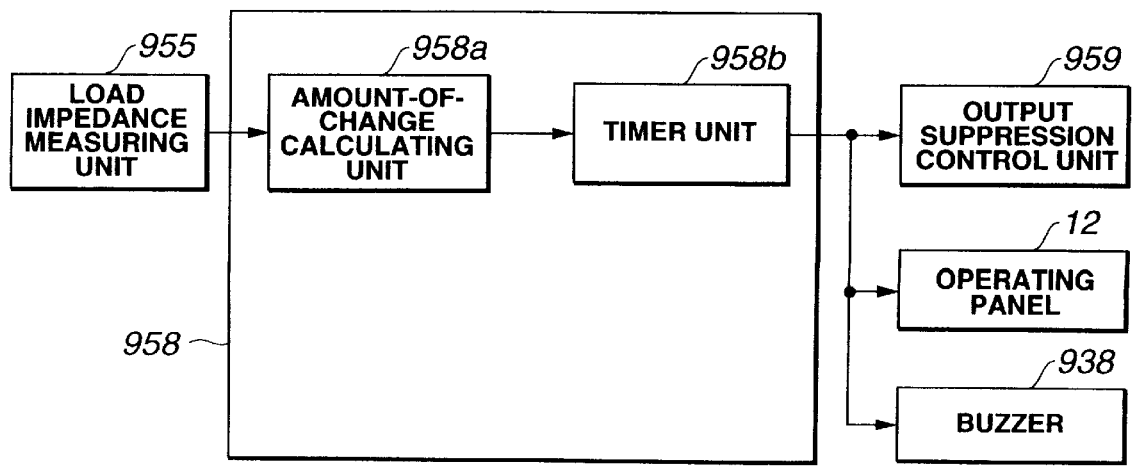
Figure 35:
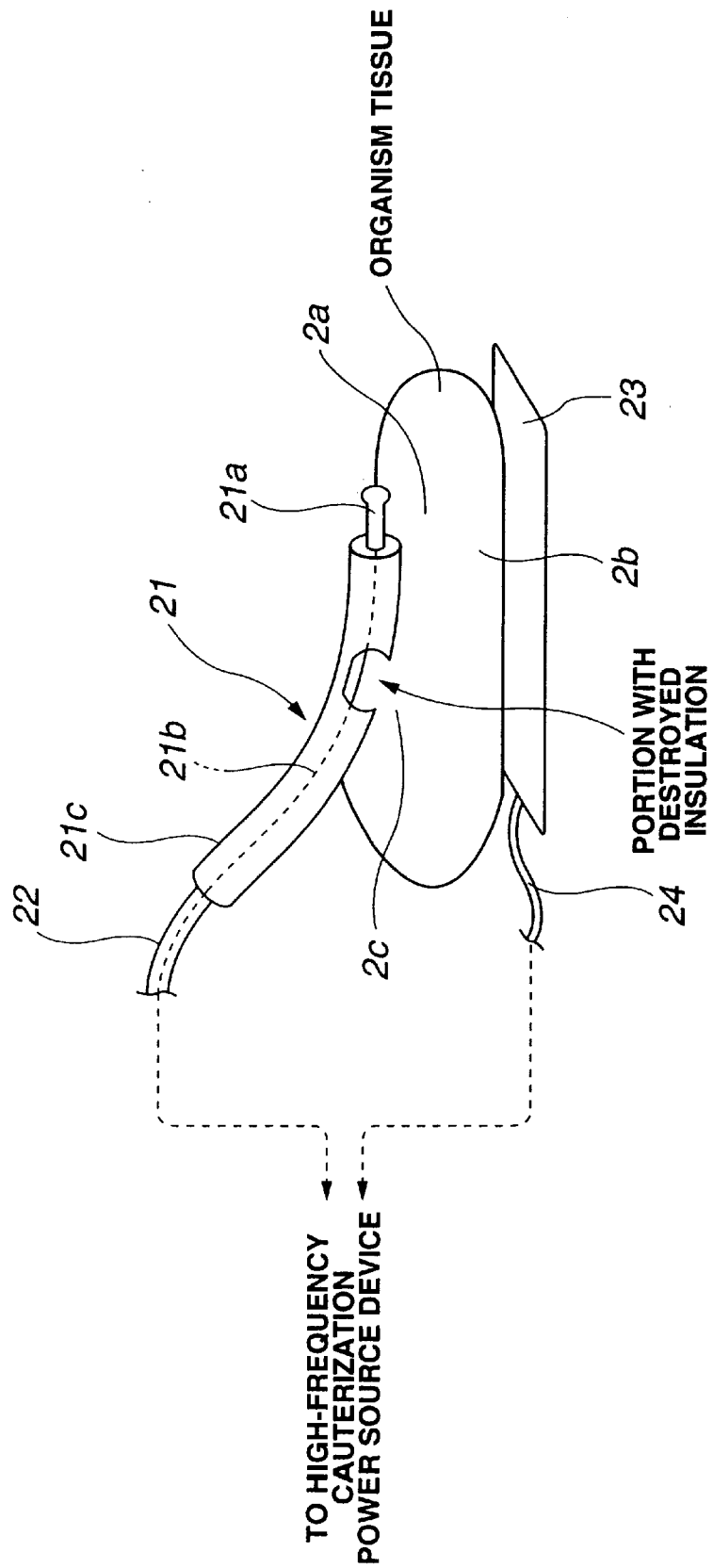
Figure 36:
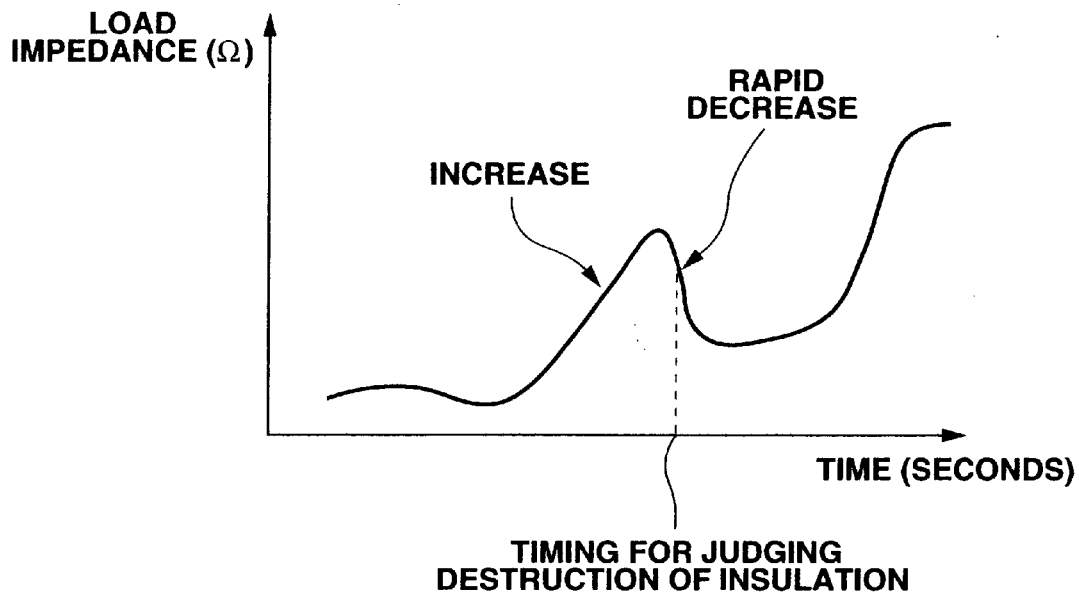
Figure 37:
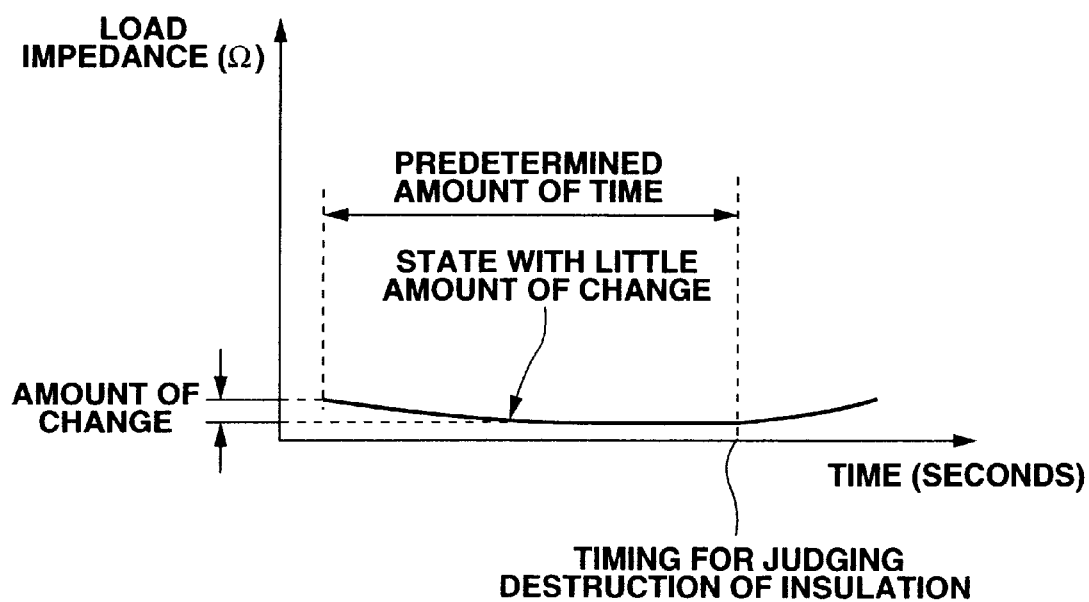

FIG; 7 is a block diagram illustrating the functional configuration of the control circuit;

FIG. 8 is an explanatory diagram illustrating the control properties switch-over timing;

FIG. 9 is an explanatory diagram illustrating the properties of output electric power as to load impedance;

FIG. 10 is an explanatory diagram illustrating the change in properties of load impedance over time;

FIGS. 11 and 12 are diagrams describing a second embodiment of the present invention;

FIG. 11 is a block diagram illustrating the configuration of the control properties judging unit;

FIG. 12 is an explanatory diagram illustrating the control properties switch-over timing;

FIG. 13 is a block diagram illustrating the configuration of a control properties judging unit according to a third embodiment of the present invention;

FIGS. 14 and 15 are diagrams describing a fourth embodiment of the present invention;

FIG. 14 is a block diagram illustrating the configuration of the control circuit;

FIG. 15 is an explanatory diagram illustrating the properties of output electric power as to load impedance;

FIG. 16 is an explanatory diagram illustrating the configuration of a parameter value input unit according to a fifth embodiment of the present invention;

FIG. 17 is an explanatory diagram illustrating the configuration of a control properties state display unit according to a sixth embodiment of the present invention;

FIGS. 18 through 20 are diagrams describing a seventh embodiment of the present invention;

FIG. 18 is an explanatory diagram illustrating the configuration of the cord type selecting unit and the constant-voltage control circuit;

FIG. 19 is an explanatory diagram illustrating the equivalency circuit of the cord of the high-frequency cauterization treating instrument;

FIG. 20 is an explanatory diagram illustrating the properties of effects on electric power loss due to the cord of the high-frequency cauterization treating instrument;

FIG. 21 is an explanatory diagram illustrating the configuration of the cord according to an eighth embodiment of the present invention;

FIG. 22 is an explanatory diagram illustrating a portion of the configuration of the cord and high-frequency cauterization power source device according to a ninth embodiment of the present invention;

FIGS. 23 through 25 are diagrams describing a tenth embodiment of the present invention;

FIG. 23 is an explanatory diagram illustrating the configuration of the operating panel;

FIG. 24 is a block diagram illustrating the configuration of the control circuit;

FIG. 25 is an explanatory diagram illustrating the properties of output electric power as to load impedance;

FIG. 26 is a block diagram illustrating the configuration of a control circuit according to an eleventh embodiment of the present invention;

FIGS. 27 and 28 are diagrams describing a twelfth embodiment of the present invention;

FIG. 27 is an explanatory diagram illustrating the configuration of the operating panel;

FIG. 28 is a block diagram illustrating the configuration of the control circuit;

FIGS. 29 through 37 are diagrams describing a thirteenth embodiment of the present invention;

FIG. 29 is a block diagram illustrating the configuration of the high-frequency cauterization power source device;

FIG. 30 is a block diagram illustrating the configuration of the voltage withstanding value input unit;

FIG. 31 is a block diagram illustrating the functional configuration of the control circuit;

FIG. 32 is a block diagram illustrating the configuration of a first insulation destruction judging unit;

FIG. 33 is a block diagram illustrating the configuration of a second insulation destruction judging unit;

FIG. 34 is a block diagram illustrating the configuration of a third insulation destruction judging unit;

FIG. 35 is an explanatory diagram illustrating an example of a treating instrument proper wherein insulation destruction has occurred;

FIG. 36 is an explanatory-diagram illustrating an example of the insulation destruction judging timing by the second insulation destruction judging unit; and FIG. 37 is an explanatory diagram illustrating an example of the insulation destruction judging timing by the third insulation destruction judging unit.

DETAILED DESCRIPTION OF THE PREFERRED EMBODIMENTS

Embodiments of the present invention will be described with reference to the drawings.

The first embodiment of the present invention will be described with reference to FIGS. 4 through 10.

Figure 1A:
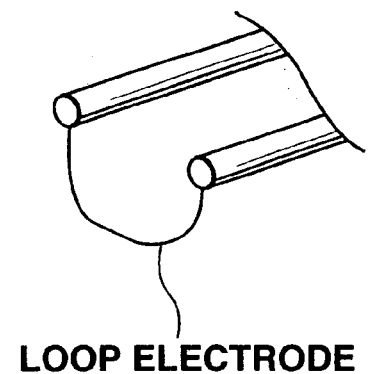
FIG. 1A is an explanatory diagram illustrating the form of a loop electrode.
Figure 1B:
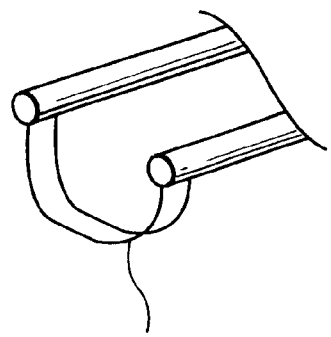
FIG. 1B is an explanatory diagram illustrating the form of a band electrode.
Figure 1C:
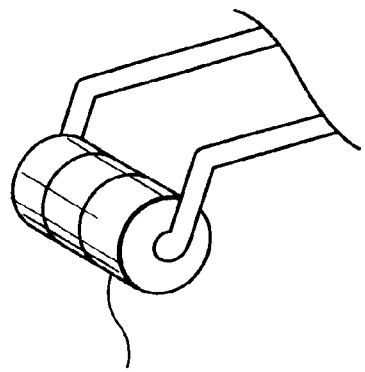
FIG. 1C is an explanatory diagram illustrating the form of a roller electrode.
Figure 2:
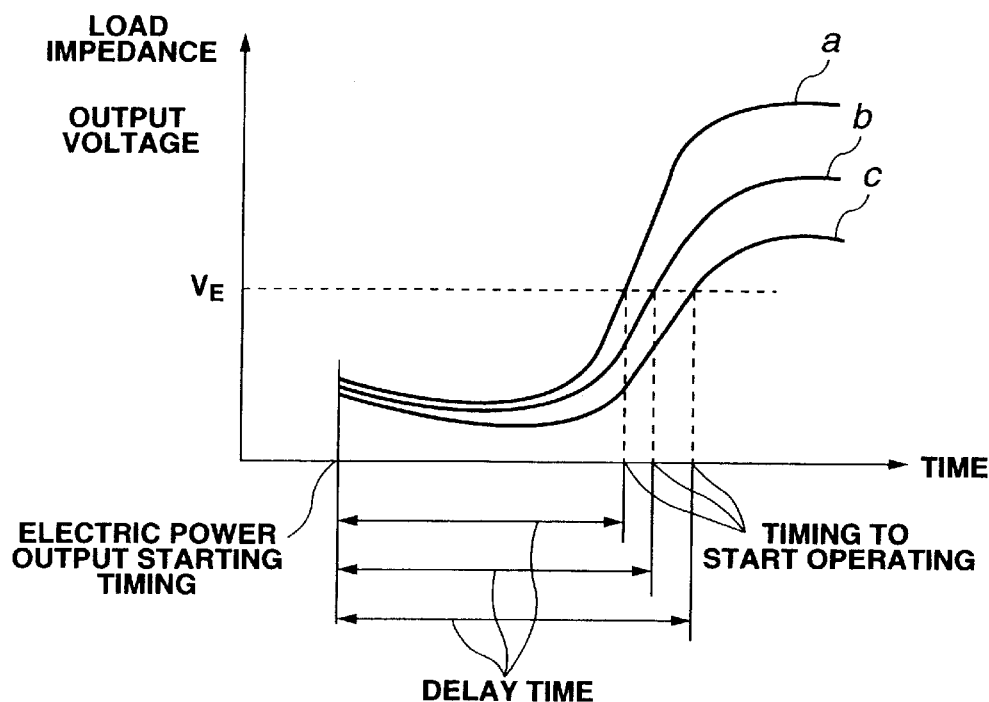
Figure 3:
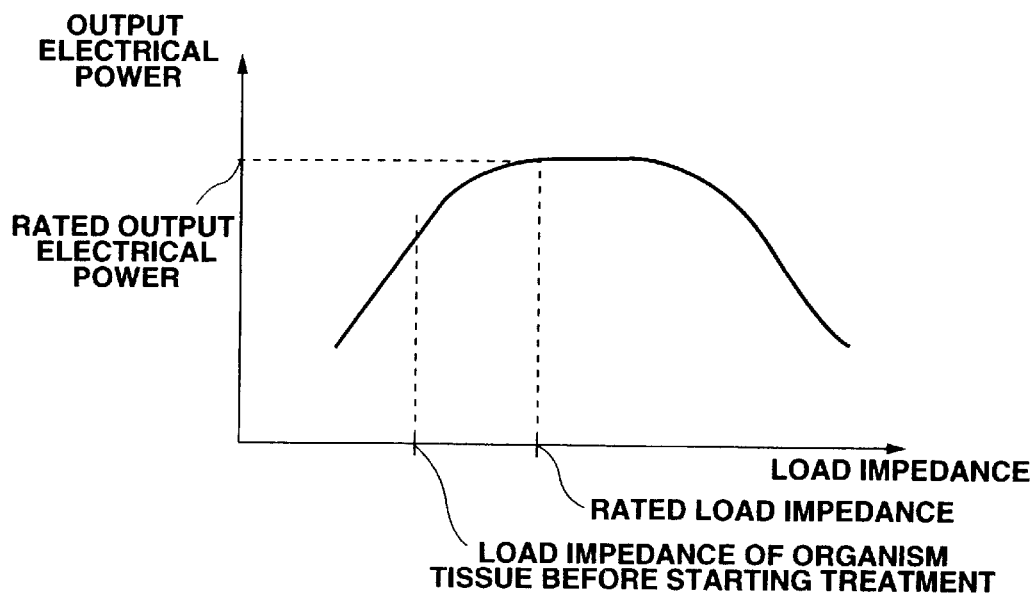
Figure 4:
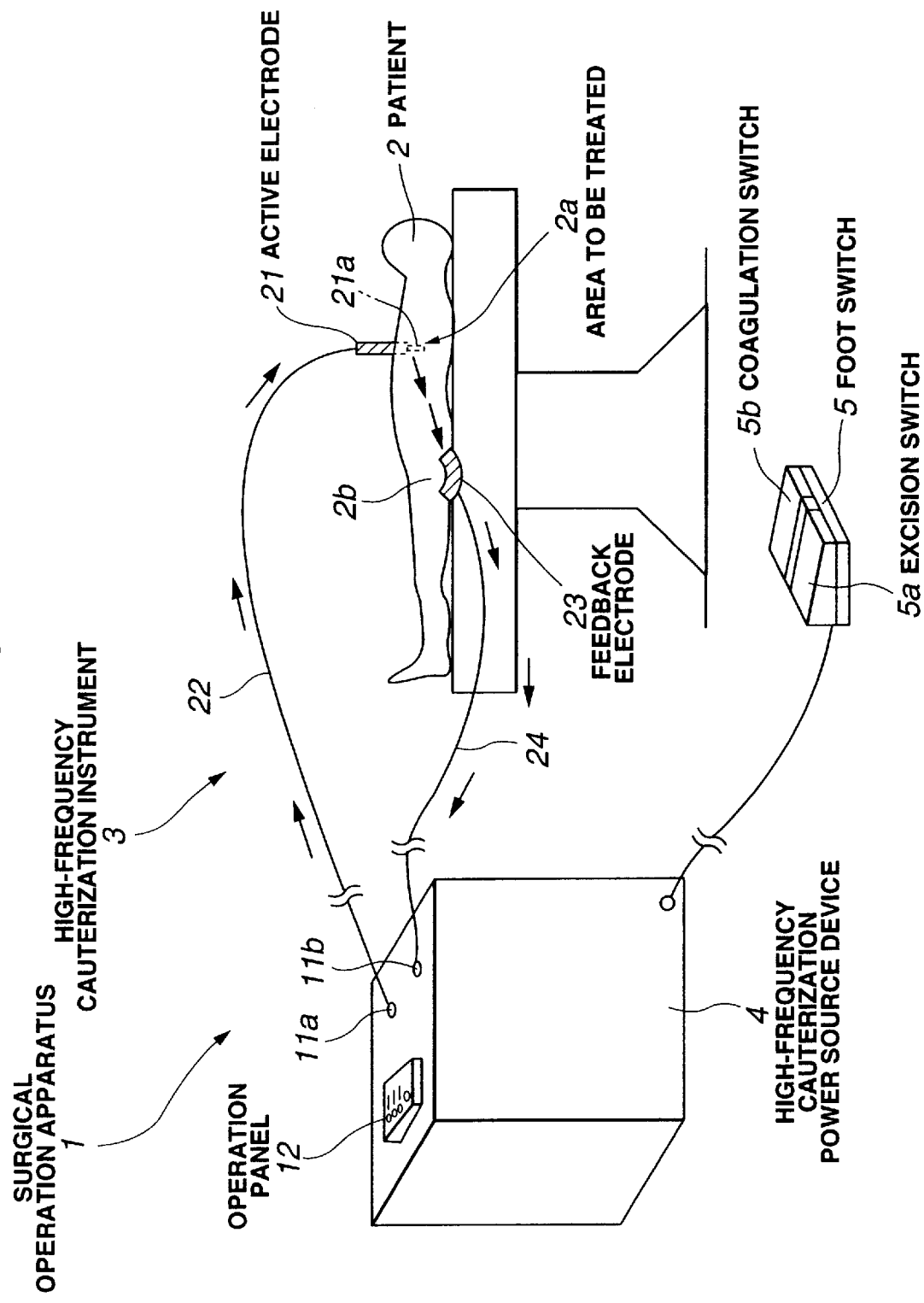
FIGS. 4 through 10 are diagrams describing a first embodiment of the present invention.

As shown in FIG. 4, the electric surgical operation apparatus 1 according to the present embodiment comprises: a high-frequency cauterization treating instrument 3 which comes into contact with the patient 2 and provides high-frequency electric power thereto, for performing excision and coagulation treatment to the area 2a to be treated; a high-frequency cauterization power source device 4 for generating high-frequency electric power to be supplied to this high-frequency cauterization treating instrument 3; and an operating switch such as a foot switch 5 connected to the high-frequency cauterization power source device 4 by an electric cable for instructing output of the high-frequency power.

The high-frequency cauterization power source device 4 has two output terminals 11a and 11b for outputting power to be supplied to the high-frequency cauterization treating instrument 3, and an operating panel 12 for performing operations such as setting the actions of this high-frequency cauterization power source device 4.

The high-frequency cauterization treating instrument 3 is a monopolar treating instrument. This monopolar treating instrument is configured of an active electrode 21 which comes into contact with the area 2a to be treated, a cord 22 extending from this active electrode 21 with the other end thereof electrically connected to the output terminal 11a, a feedback electrode portion 23 which comes in plane contact with the body surface 2b of the patient 2 at an area other than the area 2a to be treated, and a cord 24 which extends from this feedback electrode portion 23 with the other end thereof connected to the output terminal 11b.

The foot switch 5 has, for example, an excision switch 5a for instructing generating of high-frequency electric power for excision, and a coagulation switch 5b for instructing generating of high-frequency electric power for coagulation.

Incidentally, the operating foot switch is not restricted to the foot switch 5 shown in the drawings; rather, any means capable of instructing the high-frequency cauterization power source device 4 to generate high-frequency waves will suffice. That is, a configuration wherein a switch is provided to the active electrode 21, etc., will work as well.

Also, part or all of the operating panel 12 does not have to be fixed to the housing of the high-frequency cauterization power source device 4, but rather may be provided via cable, or may be provided to the operating switch or the active electrode 21.

Figure 5:
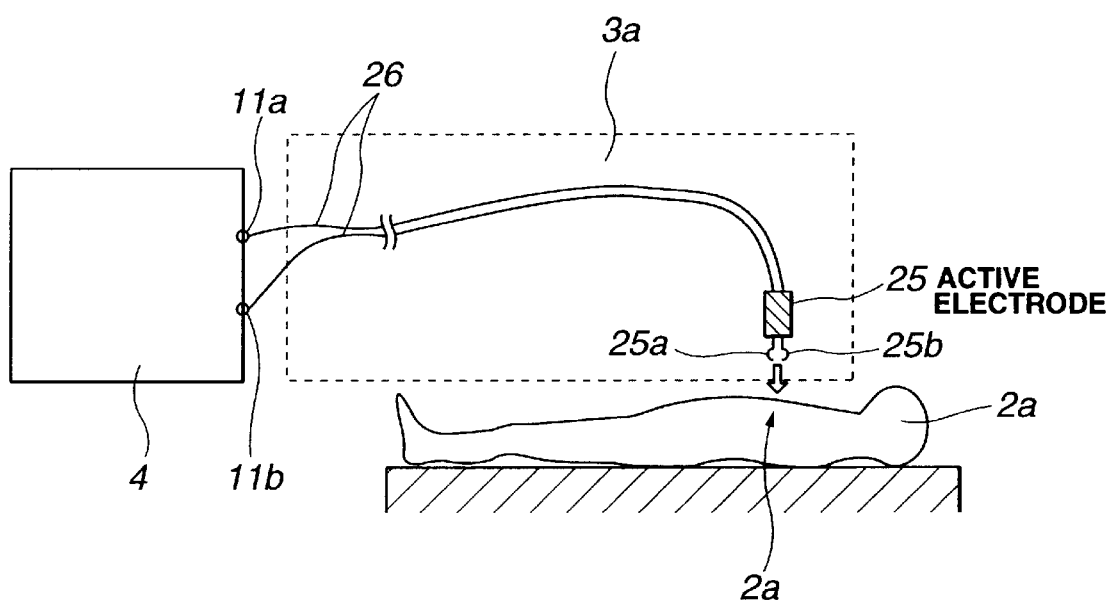

Further, the high-frequency cauterization treating instrument 3 does not have to be a monopolar treating instrument, and may be the high-frequency cauterization treating instrument 3a shown in FIG. 5 which is a bipolar treating instrument. The bipolar treating instrument shown in the figure is configured having an active electrode 25 having two electrodes 25a and 25b which come into contact with the area 2a to be treated of the patient 2, and a cord 26 extending from these two electrodes 25a and 25b with the other end thereof electrically connected to the respective output terminals 11a and 11b of the high-frequency cauterization power source device 4.

Figure 6:
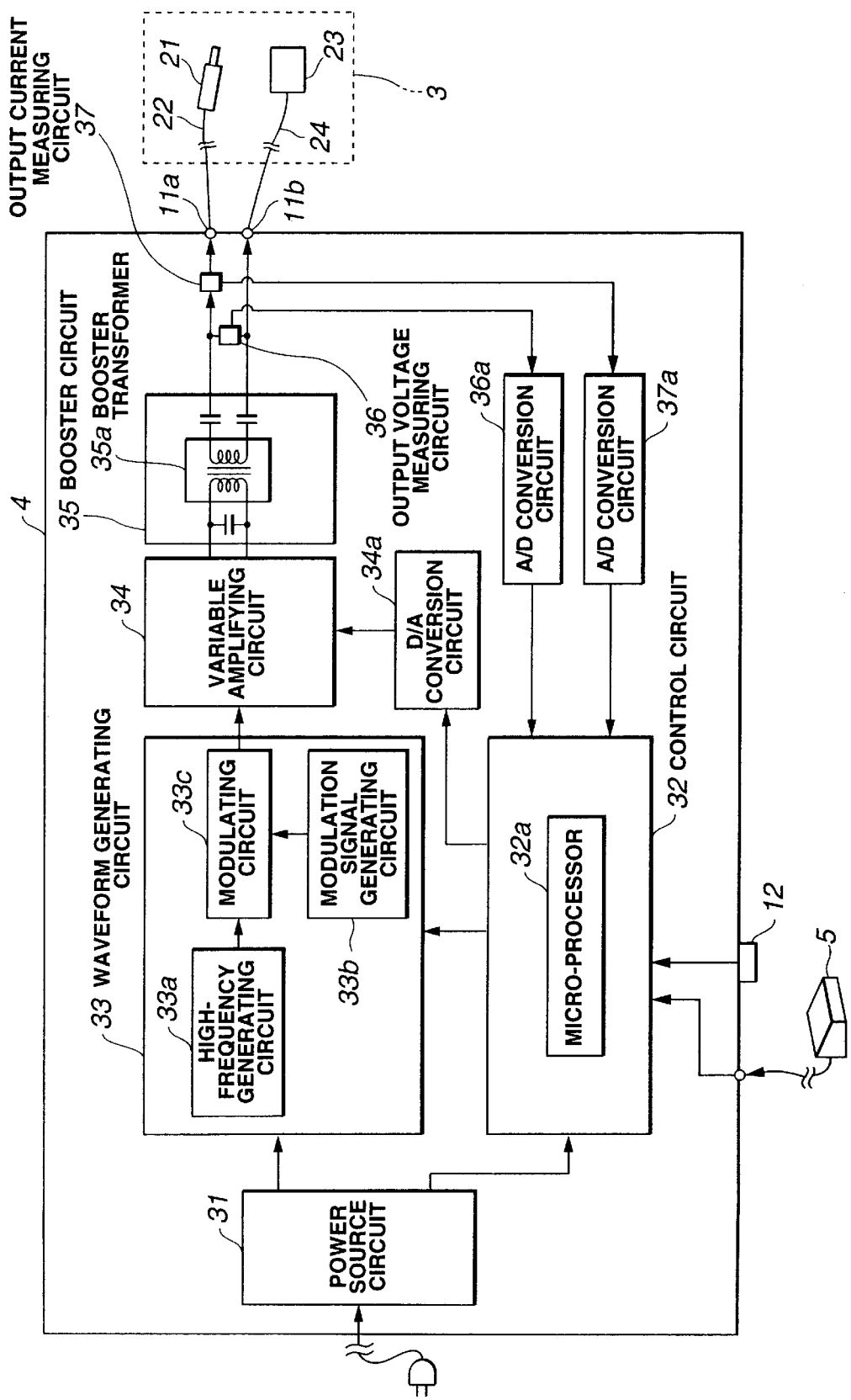

As shown in FIG. 6, the high-frequency cauterization power source device 4 is configured having a power source circuit 31, a control circuit 32, a waveform generating circuit 33, a variable amplifying circuit 34, a booster circuit 35, an output voltage measuring circuit 36, and output current measuring circuit 37, and AID conversion circuits 36a and 37a.

The electric power source circuit 31 converts electric power provided from a commercial electric power source or the like and supplies electric power to the various components of the high-frequency cauterization power source device 4. The control circuit 32 controls the various components of the high-frequency cauterization power source device 4. The waveform generating circuit 33 is controlled by the control circuit 32 and generates high-frequency waveforms to be used for treatment. The variable amplifying circuit 34 amplifies the high-frequency waves obtained from the waveform generating circuit 33 according to the gain instructed by the control circuit 32. The booster circuit 35 boosts the high-frequency waves obtained from the variable amplifying circuit 34 and outputs to the output terminals 11a and 11b. The output voltage measuring circuit 36 measures the output voltage of the high frequency waves output to the output terminals 11a and 11b from the booster circuit 35. The output current measuring circuit 37 measures the output current of the high frequency waves output to the output terminals 11a and 11b from the booster circuit 35. The A/D conversion circuits 36a and 37a perform AID conversion of the output voltage value signals obtained from the output voltage measuring circuit 36 and the output current value signals obtained from the output current measuring circuit 37, with respect to the output voltage measuring circuit 36 and output current measuring circuit 36 and output current measuring circuit 37, and provides these to the control circuit 32.

The hardware of the control circuit 32 is configured having a micro-processor 32a for example, and unshown storage devices or the like for storing programs for this micro-processor 32a to execute. Specifically, the control circuit 32 generates control signal instructing the waveformn generating circuit 33 regarding the waveform to be generated by the waveform generating circuit 33, and control signals and the like for instructing the variable amplifying circuit 34 via the D/A conversion circuit amplifying circuit 34, according to signals provided from the foot switch 5, signals provided from the operating panel 12, and signals respectively provided form the output voltage measuring circuit 36 and output current measuring circuit 37 via the A/t conversion circuits 36a and 37a.

The waveform generating circuit 33 is configured having a high-freqeuncy wave generating circuit 33a for generating high-freqeuncy waves, a modulation signal generating circuit 33b which generates excision waveform signals and coagulation waveform signals by instructions from the control circuit 32, and a modulating circuit 33c for modulating the high-freqeuncy waves obtained from the high-freqeuncy wave generating circuit 33a with the signals obtained from the modulation signal generating circuit 33b.

The booster circuit 35 is configured having a booster transformer 35a for inputting the high-frequency waves obtained from the variable amplifying circuit 34 from a primary side, and outputting the boosted high-frequency waves from the secondary side. At this time, a condenser may be provided, connected to the secondary side of this booster transformer 35a in a serial manner for removing DC components and low-frequency components. Also, a resonating condenser may be connected to the primary side of the booster transformer 35a in a parallel manner.

Figure 7:
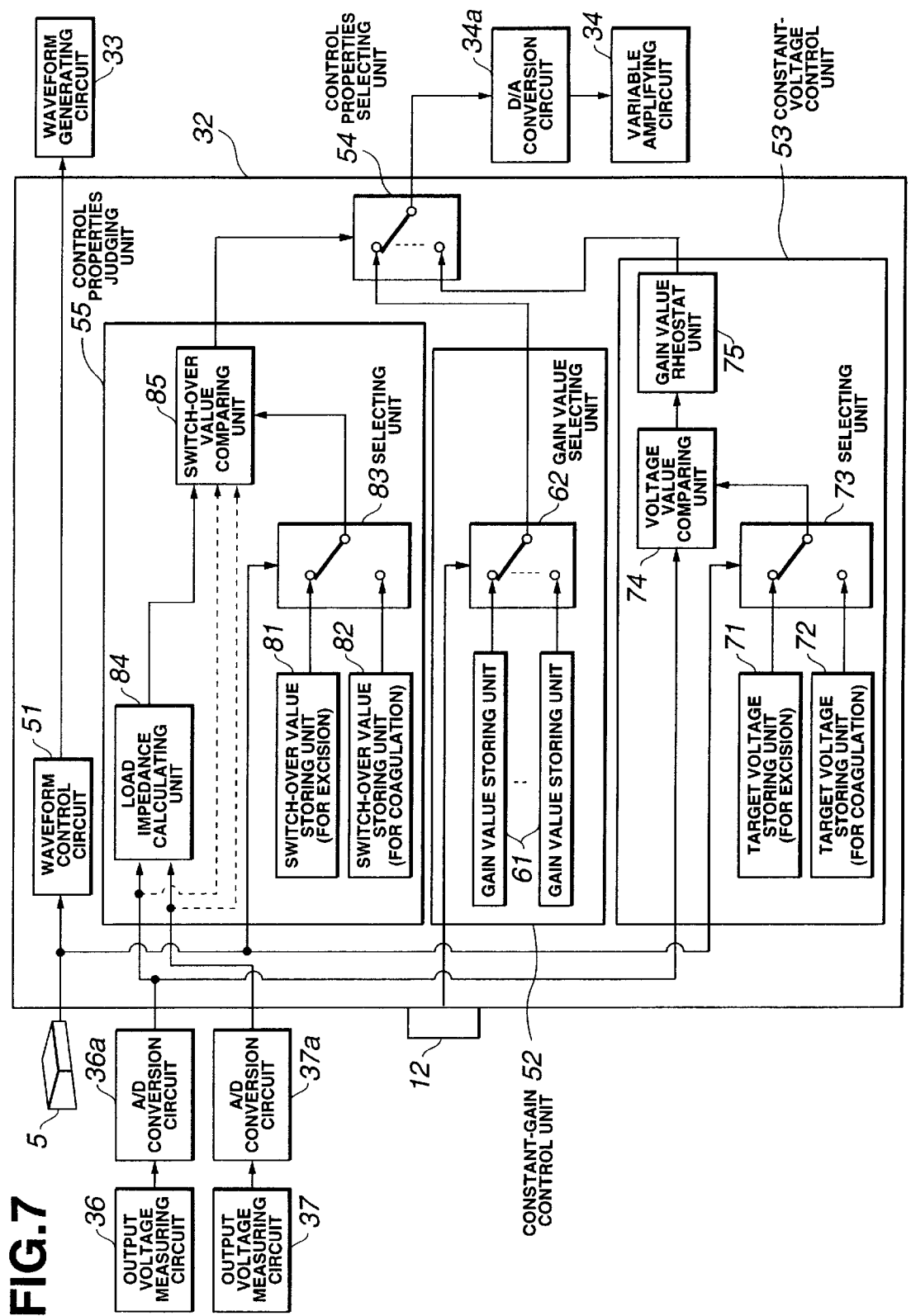

As shown in FIG. 7, the control circuit 32 is functionally configured having a waveform controlling unit 51, a constant-gain control unit 52, a constant-voltage control unit 53, a control properties selecting unit 54, and a control properties judging unit 55.

The waveform controlling unit 51 provides control signals to the waveform generating circuit 33 according to instruction signals from the foot switch 5, and controls the waveform generating circuit 33 such that high-freqeuncy waveforms corresponding to the treatment contents such as excision or coagulation are output from the waveform generating circuit 33. The constant-gain control unit 52 outputs gain signals to be provided to the variable amplifying circuit 34 corresponding to the output power level selected at the operating panel 12. The constant-voltage control unit 53 inputs output voltage value signals from the output voltage measuring circuit 36 via the A/D conversion circuit 36a, and obtains gains signals for controller the variable amplifying circuit 34 in order to maintain the output voltage from the high-frequency cauterization power source device 4 at a constant. The control properties selecting unit 54 selectively permits passage of one of the gain signals obtained with the constant-gain control unit 52 and the gain signals obtained with the constant-voltage control unit 53, and provides the passed gain signals to the variable amplifying circuit 34 via the D/A conversion circuit 34a. The control properties judging unit 55 inputs the output voltage value signals and the output current value signals obtained from the output voltage measuring circuit 36 and output current measuring circuit 37 via the A/D conversion circuits 36a and 37a, and controls the control properties selecting unit 54 for judging whether or not to allow passage of the gain signals obtained at the constant-voltage control unit 53.

The constant-gain control unit 52 is comprised having a plurality of gain value storing units 61 for storing gain values each corresponding to output power levels selected by the operating panel 12, and a gain value selecting unit 62 for selecting and outputting the gains signals from the plurality of gain value storing units 61 according to instructions from the operating panel 12.

The constant-voltage control unit 53 is comprised having a target voltage value storing unit 71 for storing a target voltage value to be maintained constant at the time of performing excision, a target voltage value storing unit 72 for storing a target voltage value to be maintained at the time of performing coagulation, a selecting unit 73 for selecting target voltage value signals from the target voltage value storing units 71 and 72 according to excision or coagulation instructions from the foot switch 5, a voltage value comparing unit 74 for detecting the difference between the output voltage value and the target voltage value selected by this selecting unit 73, and a gain value rheostat unit 75 for increasing or decreasing the gain value to be provided to the variable amplifying circuit 34, according to the output of this voltage value comparing unit 74.

The selecting unit 73 is arranged so as to select the target voltage value stored in the target voltage value storing unit 71 in the event that the excision switch 5a of the foot switch 5 is operated, and to select the target voltage value stored in the target voltage value storing unit 72 in the event that the coagulation switch 5b is operated.

The control properties judging unit 55 is comprised having a switch-over value storing unit 81 for storing a switch-over value which is an impedance value for switching over the control properties from constant-gain control to constant-voltage control at the time of excision, a switch-over value storing unit 82 for storing a switch-over value which is an impedance value for switching over the control properties from constant-gain control to constant-voltage control at the time of coagulation, a selecting unit 83 for selecting a switch-over value from the switch-over value storing units 81 and 82 according to excision or coagulation instructions from the foot switch 5, a load impedance calculating unit 84 for taking the output voltage value signals and the output current value signals obtained from the output voltage measuring circuit 36 and output current measuring circuit 37 via the A/D conversion circuits 36a and 37a and subjecting these to division for example, thereby calculating load impedance, and a switch-over value comparing unit 85 for comparing the load impedance obtained by the load impedance calculating unit 84 with the switch-over value that has passed through the selecting unit 83, and controls the control properties selecting unit 54 according to the relation of these size-wise.

The selecting unit 83 is arranged so as to select the switch-over value stored in the switch-over value storing unit 81 in the event that the excision switch 5a of the foot switch 5 is operated, and to select the switch-over value stored in the switch-over value storing unit 82 in the event that the coagulation switch 5b is operated.

Incidenrtally, the values to be compared at the switch-over value comparing unit 85 are not restricted to impedance values, and may be the output voltage value or output current value instead. At this time, the switch-over values stored in the switch-over value storing units 81 and 82 are the voltage value or current value instead of the impedance value.

Also, in the event that the values to be compared at the switch-over value comparing unit 85 are not impedance values, the load impedance calculating unit 84 becomes unnecessary. Accordingly, in the event that the load impedance becomes greater than a predetermined value, or in the event that the output voltage value becomes greater than a predetermined value, or in the event that the output current value becomes smaller than a predetermined value, the control properties judging unit 55 controls the control properties selecting unit 54 so as to switch the control properties from constant-gain control to constant-voltage control.

The operation of the electric surgical operation apparatus configured as described above will now be described.

The operation regarding the excision process will be described first.

First, the output power level is set using the operating panel 12. Now, the output power level is indicated by the output power value at the time of rated load impedance, for example. The output power value at the time of rated load impedance is a value such as 150 W, 200 W, 250 W, and so forth.

Once the output voltage level is set with the operating panel 12, the gain value selecting unit 62 of the constant-gain control unit 52 selects and outputs a gain value from the gain values stored in the multiple gain value storing units 61, corresponding to the output voltage level set at the operating panel 12. Then, signals indicating this gain value are sent to the variable amplifying circuit via the control properties selecting unit 54 and the D/A conversion circuit 34a. Incidentally, in the initial state, the control properties selecting unit 54 allows passage of gain value signals from the constant-gain control unit 52.

Next, once the output voltage level has been set with the operating panel 12, the active electrode 25 of the high-frequency cauterization treating instrument 3 is brought into contact with the area 2a to be treated. Further, the excision switch 5a of the foot switch 5 is operated. Consequently, the waveform controlling unit 51 provides instructions to the waveform generating circuit 33 so as to generate excision high-frequency waves, and the waveform generating circuit 33 provides the excision high-frequency waves to the variable amplifying circuit 34. This variable amplifying circuit 34 amplifies the high-frequency waves following the gain value provided from the constant-gain control unit 52. The high-frequency waves are boosted at the booster circuit 35, and provided to the high-frequency cauterization treating instrument 3 via the output terminals 11a and 11b.

Thus, the high-frequency current concentratedly flows into the organism tissue at the area 2a to be treated, from the active electrode 21 of the high-frequency cauterization treating instrument 3. The high-frequency current that has flown in is dispersed and recovered by the feedback electrode portion 23 which is in plane contact with body surface 2b other than the area 2a to be treated. At this time, the area 2a to be treated is heated by heat owing to the high-freqeuncy current that has flown in through the area 2a to be treated, and the heat transmitted from the active electrode 21 which has generated heat due to the high-freqeuncy current. Incidentally, the area 2a to be treated in contact with the active electrode 25 is heated as well in the event that the high-frequency cauterization treating instrument 3a is used instead of the high-frequency cauterization treating instrument 3.

At the point in time that the heating is started, the organism tissue at the area 2a to be treated contains a great deal of moisture, so the impedance in the organism tissue, i.e., the load impedance, is in a low state. As the heating gradually progresses, the liquid and the like in the cells of the organism tissue become ionized. Thus, the load impedance temporarily drops, as shown in FIG. 8, following which the moisture and the like such as the liquid and the like in the cells evaporate, tissue deterioration proceeds, and the increase of the load impedance begins.

When the load impedance value increases, the output voltage value of high-freqeuncy waves output from the high-frequency cauterization power source device 4 increases, and the output current value decreases.

The output voltage value and the output current value are respectively measured by the output voltage measuring circuit 36 and output current measuring circuit 37, and provided to the control circuit 32 via the A/D conversion circuits 36a and 37a. The load impedance calculating unit 84 of the control properties judging unit 55 of this control circuit 32 subjects the provided output voltage value and output current value to division for example, thereby calculating the load impedance value, and provides this value to the switch-over value comparing unit 85. The switch-over value comparing unit 85 compares the load impedance value with the switch-over impedance value stored in the switch-over value storing unit 81, and controls the control properties selecting unit 54 such that the gain signals from the constant-gain control unit 52 are selected until the load impedance value exceeds the switch-over impedance value. Then, in the event that the load impedance value exceeds the switch-over impedance value, the control properties selecting unit 54 is controlled such that the gain value signals from the constant-voltage control unit 53 are selected.

Incidentally, the load impedance value is small during the predetermined period from the starting of heating the organism tissue of the area 2a to be treated, so the control properties judging unit 55 controls the control properties selecting unit 54 so as to select the gain value signals from the constant-gain control unit 52, and the high-frequency cauterization power source device 4 performs constant-gain control. That is, the control properties judging unit 55 is a means for detecting the state of tissue deterioration of the organism tissue, and controlling the switching of control properties.

During the period in which constant-gain control is performed with the present embodiment, control is made for maintaining none of the output voltage, output current, nor output power at a constant, so as shown in FIGS. 8 and 9, the output voltage value, output current value, and output power value change according to changes in the rated load impedance value.

Also, as shown in FIG. 9, the output power value reaches the output power level set at the operating panel 12, i.e., the maximum output power value, at the time that the load impedance nears the rated load impedance, and the output power value decreases as the load impedance departs from the load impedance.

Then, with the output power level set at the operating panel 12 at 150 W, 200 W, or 250 W, for example, the output power value at the time of rated load impedance is the value of 150 W, 200 W, or 250 W.

It should be noted that in the present embodiment, constant-gain control means that the output gain of the variable amplifying circuit 34 is not controlled in regard to changes in the load impedance value, and does snot necessarily mean that the output gain of the variable amplifying circuit 34 has to be aggressively maintained at a constant. Also, while constant-voltage control is being performed, the constant-gain control according to the present Application does not necessarily have to be performed; rather, control may be performed such that at least one of the output value and output current value are controlled so as to be maintained constant, for example.

Once the load impedance value increases and attains the switch-over impedance value, and reaches the control properties switch-over timing, switch-over value comparing unit 85 of the control properties judging unit 55 which has detected this state controls the control properties selecting unit 54 so as to select the gain value from the constant-voltage control unit 53, and constant-voltage control is started.

That is, at the constant-voltage control unit 53, the output voltage value and the target voltage value stored in the target voltage value storing unit 71 are compared by the voltage value comparing unit 74, and the gain value rheostat unit 75 increases or decreases the gain value so that the output voltage value and the target voltage value agree. Providing this signal indicating gain value to the variable amplifying circuit 34 via the control properties selecting unit 54 and D/A conversion circuit 34a maintains the output voltage of the high-frequency cauterization power source device 4 constant. Accordingly, as shown in FIG. 8, following the control properties switch-over timing, the output voltage value is maintained at the target voltage value.

At this time, in the period before the control properties switch-over timing, the amount of heating to the organism tissue of the area 2a to be treated differs according to the output power level set at the operating panel 12, so the speed of moisture and the like evaporating from the organism tissue differs. Accordingly, as shown in FIG. 10, in the event that the output power level is small, the speed of increase of the load impedance is slower in comparison with cases wherein the output power level is great, and the speed reaching the switch-over load impedance value is slower.

On the other hand, in the period following the control properties switch-over timing, the constant-voltage control unit 53 performs constant-voltage control according to the target voltage value stored in the target voltage value storing unit 71 regardless of the output power level set in the operating panel 12. Accordingly, even in the case that the output power differs at the time of constant-gain control as shown in FIG. 9, the output power is the same at the time of constant-voltage control.

Incidentally, judgment of the control properties switch-over timing with the control properties judging unit 55 is not restricted to performing comparison between the load impedance value and the switch-over impedance value; rather, comparison may be made between the output voltage value and the switch-over voltage value as shown in FIG. 8, or comparison may be made between the output current value and the switch-over current value.

On the other hand, once the output voltage reaches the ,predetermined voltage value, arc discharge to the organism tissue at the area 2a to be treated starts by the active electrode or the active electrode 25. The excision process is performed on the organism tissue at the area 2a to be treated by this arc discharge.

Accordingly, the target voltage value to be stored in the target voltage value storing unit 71 should be greater than the voltage value for starting arc discharge, and small enough so as to not excessively intrude into the organism tissue. Specifically, this target voltage value is around 200 V to 300 V, for example.

That is, maintaining the output voltage value at such a target voltage value stabilizes the excision by preventing excessively small voltage, and excessive intrusion into the organism tissue is prevented by preventing excessively great voltage. Also, following the control properties switch-over timing the output voltage value is maintained at a constant target voltage value regardless of the set output power level. Incidentally, the switch-over value to be stored in the switch-over value storing unit 81 may be a switch-over value that corresponds to a voltage near the target voltage value or a voltage lower than the target voltage value by a certain margin.

Next, the operation regarding to the coagulation process will be described.

First, the coagulation switch 5b of the foot switch 5 is operated. Consequently, the waveform controlling unit 51 provides signals to the waveform generating circuit 33 so as to generate coagulation high-frequency waves, and the waveform generating circuit 33 provides the high-frequency waves modulated to for example an intermittent waveform for coagulation, to the variable amplifying circuit 34. This variable amplifying circuit 34 amplifies the high-frequency waves following the gain value provided from the constant-gain control unit 52, as with the case of the excision process. The high-frequency waves are boosted at the booster circuit 35, and provided to the high-frequency cauterization treating instrument 3 or the high-frequency cauterization treating instrument 3a via the output terminals 11a and 11b.

Thus, as with the case of the excision process, the organism tissue at the area 2a to be treated is heated by the to the high-frequency cauterization treating instrument 3 or the high-frequency cauterization treating instrument 3a, increase of load impedance starts, and output voltage increases.

Then in the case of the coagulation process, once the load impedance value or output voltage or output current reaches a the stored value stored in the switch-over value storing unit 82, the control properties switch over to constant-voltage control, and the output voltage value is maintained to the target voltage value stored in the target voltage value storing unit 72.

The target voltage value to be stored in the target voltage value storing unit 72 should be great enough to generate coagulation, and small enough so as to not cause arc discharge or excision owing to arc discharge. This target voltage value is smaller than the voltage value stored in the target voltage value storing unit 71, for example.

That is, maintaining the output voltage value at such a target voltage value stabilizes the excision by preventing excessively small voltage, and intrusion into the organism tissue is prevented by preventing excessively great voltage. Also, as with the case of excision, following the control properties switch-over timing, the output voltage value is maintained at a constant target voltage value regardless of the set output power level. Incidentally, the switch-over value to be stored in the switch-over value storing unit 82 may be a switch-over value may correspond to a voltage near the target voltage value or a voltage lower than the target voltage value by a certain margin.

As described above, according to the present embodiment, the voltage for excision is maintained at a constant appropriate voltage value regardless of the setting of output power at the time of the excision process, meaning that stable excision can be performed, and excessive intrusion can be prevented.

Also, the voltage for coagulation is maintained at a constant appropriate voltage value regardless of the setting of output power at the time of the coagulation process, meaning that stable coagulation can be performed, and arc discharge or intrusion due to excision by arc discharge can be prevented.

According to such, stable and unintrusive excision and coagulation operation can be performed, even in the event that output power settings are changed.

Also, the switching over between constant-voltage control and other control state is judged according to the state of tissue deterioration, so transfer can be made to constant-voltage control before the load impedance of the organism tissue reaches an appropriate value for excision or coagulation, and cancellation of the constant-voltage control state during excision or coagulation can be prevented.

Accordingly, constant-voltage control can be appropriately performed according to the tissue deterioration state, and stable and unintrusive excision and coagulation operation can be performed. Also, output power can be adjusted, so the time from operating the foot switch to starting the excision or coagulation operation can be adjusted, thus greatly improving the operability.

A second embodiment of the present invention will be described with reference to FIGS. 11 and 12. Incidentally, the following description is mainly a description regarding the points which differ from the above first embodiment, so components that are the same as those in the first embodiment will be denoted by the same reference numerals and description thereof will be omitted.

In the present embodiment, the configuration of the control properties judging unit 101 shown in FIG. 11 differs from the configuration of the control properties judging unit 55 of the first embodiment shown in FIG. 7.

That is, the configuration of the control properties judging unit 101 comprises a rate-of-change calculating unit 102 for calculating the rate of change of the load impedance value or output voltage value or output current value as to time, provided before the switch-over value comparing unit 85.

Also, instead of the switch-over load impedance value or switch-over voltage value or switch-over current value being stored in the switch-over value storing units 81 and 82, the switch-over impedance rate of change which is the impedance rate of change at the time of switching control properties, or switch-over voltage rate of change which is the voltage rate of change at the time of switching control properties, or switch-over current rate of change which is the current rate of change at the time of switching control properties, are used.

The operation of the present embodiment configured thus will now be described. Incidentally, with the present embodiment, the points differing from the first embodiment are described.

The output voltage value and the output current value respectively measured by the output voltage measuring circuit 36 and output current measuring circuit 37 are provided to the load impedance calculating unit 84 via the A/D conversion circuits 36*a* and 37*a*. The load impedance value calculated at the load impedance calculating unit 84 is provided to the rate-of-change calculating unit 102. This rate-of-change calculating unit 102 calculates the load impedance rate of change which is the rate of change of the provided load impedance value as to time, and provides this value to the switch-over value comparing unit 85.

The switch-over value storing units 81 and 82 respectively store the switch-over impedance rates of change which is the threshold value for switching control properties to constant voltage control, at the time of performing excision and at the time of performing coagulation. Then, the selecting unit 83 selects a switch-over impedance rate of change from the switch-over value storing units 81 and 82 by signals from the foot switch 5 indicating whether excision or coagulation, and provides this to the switch-over value comparing unit 85.

Thus, the switch-over value comparing unit 85 compares the load impedance rate of change and the switch-over impedance rate of change, and, as shown in FIG. 12, upon detecting the load impedance rate of change exceeding the switch-over impedance, controls the control properties selecting unit 54 so as to transfer control properties to constant-voltage control, with this timing as the control properties switch-over timing. This takes advantage of the properties wherein the load impedance and output voltage and output current greatly change due to tissue deterioration near the control properties switch-over timing, as shown in FIG. 8.

Also, judgment of the control properties switch-over timing is not limited to the load impedance rate of change exceeding the switch-over impedance rate of change; this may be judged by the output voltage rate of change or output current rate of change exceeding the switch-over voltage rate of change or switch-over current rate of change. In this case, the rate-of-change calculating unit 102 is provided with output voltage value or output current value instead of the load impedance value, and the switch-over value storing units 81 and 82 store the switch-over voltage value or switch-over current value.

According to the above-described embodiment, in addition to the advantages of the first embodiment, judgment of the control properties switch-over timing is made according to the load impedance value rate of change or output voltage value rate of change or output current value rate of change, so the response of switching the control properties over can be speeded up as compared to cases wherein judgment is made according to the load impedance value or output voltage value or output current value.

A third embodiment will be described with reference to FIG. 13. Incidentally, the following description is mainly a description regarding the points which differ from the above second embodiment, so components that are the same as those in the second embodiment will be denoted by the same reference numerals and description thereof will be omitted.

The control properties judging unit 151 according to the present embodiment shown in the Figure does away with the switch-over value storing units 81 and 82, selecting unit 83, and the switch-over value comparing unit 85 shown in FIG. 11 with the above second embodiment. Instead, a rate-of-change calculating unit 152 and extremum judging unit 153 are provided behind the rate-of-change calculating unit 102.

The rate-of-change calculating unit 152 calculates the secondary differential coefficient, which is the further rate of change as to time of the primary differential coefficient, i.e., the load impedance rate of change or output voltage rate of change or output current rate of change obtained from the rate-of-change calculating unit 102. The extremum judging unit 153 detects the extremum of the primary differential coefficient from the secondary differential coefficient obtained with the rate-of-change calculating unit 152 to judge the control properties switch-over timing, and thereby controls the later control properties selecting unit 54.

The operation of the present embodiment configured thus will now be described. Incidentally, with the present embodiment, the points differing from the second embodiment are described.

The primary differential coefficient, i.e., the load impedance rate of change or output voltage rate of change or output current rate of change obtained from the rate-of-change calculating unit 102, is provided to the rate-of-change calculating unit 152. Then, the rate-of-change calculating unit 152 calculates the rate of change of the provided primary differential coefficient as to time, i.e., a secondary differential coefficient, and provides this to the extremum judging unit 153. The extremum judging unit 153 performs judging of the provided secondary differential coefficient, and in the event that detection is made that this value has become smaller than a predetermined threshold value, this is determined to be the extremum of the primary differential coefficient. Next, the timing at which the extremum of the primary differential coefficient was determined is judged to be the control properties switch-over timing, and the control properties selecting unit 54 is controlled so as to switch the control properties over to constant-voltage control. This takes advantage of the properties wherein the load impedance rate of change and output voltage rate of change and output current rate of change attain an extremum near the control properties switch-over timing, as shown in FIG. 12.

According to the above-described present embodiment, in addition to the advantages of the second embodiment, judgment depending on excision or coagulation is unnecessary at the time of judging the control properties switch-over timing. In other words, the switch-over value storing units 81 and 82 and the selecting unit 83 can be done away with, thereby simplifying the circuit configuration and control structure.

Also, a threshold value corresponding to the treating instrument properties is not used at the time of judging the control properties switch-over timing, so the control properties switch-over timing can be judged regardless of the properties of the treating instrument, thus greatly improving general usability.

A fourth embodiment of the present invention will be described with reference to FIGS. 14 and 15. Incidentally, the following description is mainly a description regarding the points which differ from the above first embodiment, so components that are the same as those in the first embodiment will be denoted by the same reference numerals and description thereof will be omitted.

In the present embodiment, the configuration of the control circuit 201 shown in FIG. 14 differs from the configuration of the control circuit 32 of the first embodiment shown in FIG. 7.

That is, in comparison with the control circuit 32 of the first embodiment, the control circuit 201 comprises a constant-power control unit 202 for outputting gain values to be provided to the variable amplifying circuit 34 so as to alleviate change in output electric power as to the change in load impedance, a control properties selecting unit 203 which selects gain values from the constant-gain control unit .52 and constant-voltage control unit 53 and constant-power control unit 202 instead of the control properties selecting unit 54 which selects gain values from the constant-gain control unit 52 and constant-voltage control unit 53, and a control properties judging unit 204 for controlling the control properties selecting unit 203 instead of the control properties judging unit 55 shown in FIG. 7.

The constant-power control unit 202 comprises an output power calculating unit 211 which obtains output power values by subjecting the output voltage value and output current value provided from the output voltage measuring circuit 36 and output current measuring circuit 37 via the A/D conversion circuits 36a and 37a to multiplication or the like, a power value comparing unit 212 for comparing the output power values obtained by this output power calculating unit 211 with output power level setting values input form the operating panel 12, and a gain value arheostat unit 213 for increasing or reducing the gain value according to the comparison results of this power value comparing unit 212 so as to maintain the output power value at the output power level setting value.

The control properties judging unit 204 further comprises switch-over value storing units 221 and 222 for storing threshold values for switching over control properties from constant-gain control to constant-power control at the time of excision and coagulation respectively, in addition to the control properties judging unit 55 shown in FIG. 7 with the first embodiment, and a selecting unit 223 for selecting stored values from the switch-over value storing units 221 and 222 according to excision or coagulation signals from the foot switch 5, while, instead of the switch-over value comparing unit 85 shown in FIG. 7 with the first embodiment, a switch-over value comparing unit 224 is provided for judging the switch-over timing from constant-gain control to constant-power control and the switch-over timing from constant-power control to constant-voltage control, thereby controlling the control properties selecting unit 203.

The operation of the present embodiment configured thus will now be described. Incidentally, with the present embodiment, the points differing from the first embodiment are described.

In the event that the load impedance value obtained by the load impedance calculating unit 84 of the control properties judging unit 204 exceeds the switch-over value selected by the selecting unit 223, the switch-over value comparing unit 224 upon detecting this controls the control properties selecting unit 203 so as to switch over the control properties from constant-gain control to constant-power control.

Then, as shown in FIG. 15, control properties transfer from the constant-gain control region to the constant-power control region. When under constant-power control, the output power is maintained at the output power level set at the operating panel 12, for example.

Also, in the event that the load impedance value exceeds the switch-over value selected by the selecting unit 83, the switch-over value comparing unit 224 upon detecting this controls the control properties selecting unit 203 so as to switch over the control properties from constant-power control to constant-voltage control. Then, as shown in FIG. 15, control properties transfer from the constant-power control region to the constant-voltage control region. The properties of the constant-voltage control are the same as those in the first embodiment.

Also, as with the first embodiment, the switch-over value is not restricted to load impedance values, and may be output voltage values or output current values.

According to the present embodiment described above, in addition to the advantages of the first embodiment, constant-power control is performed before transferring to constant-voltage control, so the electric power for heating the organism tissue is maintained so as to not change as to change in the load impedance, thereby reducing the change in time required for tissue deterioration depending on difference on parts of the organism tissue, consequently improving operability.

Also, though the present embodiment has been configured to transfer the control properties from constant-gain control to constant-power control to constant-voltage control, the constant-gain control may be omitted and the embodiment be configured to transfer the control properties from constant-power control to constant-voltage control.

A fifth embodiment of the present invention will be described with reference to FIG. 16. Incidentally, the following description is mainly a description regarding the points which differ from the above first embodiment, so components that are the same as those in the first embodiment will be denoted by the same reference numerals and description thereof will be omitted.

With the present embodiment, the operating panel 12 shown in FIG. 5 for example is provided with a parameter value input unit 301 shown in the Figure for providing input of values to the switch-over value storing units 81 and 82 and the target voltage value storing units 71 and 72 shown in FIG. 7 with the first embodiment.

The parameter value input unit 301 is configured having parameter value display units 302 for displaying the values for each of the parameters, such as switch-over values for excision and coagulation, target voltage values, etc., and parameter value increasing/decreasing buttons 303 for increasing or decreasing parameter values by depressing, for example.

The operation of the present embodiment will now be described. Incidentally, with the present embodiment, the points differing from the first embodiment are described.

The parameter values are displayed on the parameter value display units 302. Operating the parameter value increasing/decreasing buttons 303 corresponding to the parameter value display units 302 increases or decreases the parameter values displayed on the parameter value display units 302, and these displayed parameter values are set in the switch-over value storing units 81 and 82 and the target voltage value storing units 71 and 72.

Incidentally, the parameter value input unit 301 according to the present embodiment is not restricted to being added to the first embodiment, and rather may also be added to the second embodiment and third embodiment. In the event of adding the parameter value input unit 301 to the third embodiment, the values of the switch-over value storing units 221 and 222 shown in FIG. 14 may be set by the parameter value input unit 301.

According to the present embodiment described above, in addition to the advantages of the first through third embodiments, the parameter values can be set easily, so changes in the type of treating instruments used can be easily dealt with. Also, the parameter values can be easily set according to the operating senses of each of multiple operators. Further, the parameter values as shown in on the parameter value input unit, so the current setting states for the parameter values can be easily recognizes. Thus, the operability improves.

Incidentally, the configuration of the parameter value input unit 301 is not restricted to the configuration shown in FIG. 16; rather, this may be configured of an unshown keyboard or a monitor device having similar functions, and so forth.

A sixth embodiment of the present invention will be described with reference to FIG. 17. Incidentally, the following description is mainly a description regarding the points which differ from the above first embodiment, so components that are the same as those in the first embodiment will be denoted by the same reference numerals and description thereof will be omitted.

With the present embodiment, the operating panel 12 shown in FIG. 5 for example is provided with a control properties state display unit 401 which displays the current control properties state.

The control properties state display unit 401 comprises display lamps 402 indicating whether the current control properties are set at constant-gain control or constant-voltage control.

The operation of the present embodiment configured thus will now be described. Incidentally, with the present embodiment, the points differing from the first embodiment are described.

The control circuit 32 shown in FIG. 7 has information of the current control properties state, and this information of the current control properties state is provided from this control circuit 32 to the control properties state display unit 401. Thus, the display lamp 402 corresponding to the control properties state is lit. Accordingly, the operator can easily tell whether the current control properties are set at constant-gain control or constant-voltage control.

Incidentally, the control properties state display unit 401 according to the present invention is not restricted to being provided to the operating panel 12, and can instead be displayed on an unshown monitor device or the like, for example.

Also, the control properties state display unit 401 according to the present embodiment is not restricted to being added to the first embodiment, and rather may also be added to the second embodiment and third embodiment. In the event of adding the control properties state display unit 401 to the third embodiment, a state of constant-power control may be displayed as a control properties state. Also, in the event that constant-current control is to be performed, a state of constant-current control may be displayed.

Further, instead of providing means such as the control properties state display unit 401 wherein the technician is informed of the control properties state in a visual manner, unshown means may be provided wherein the operator is informed of the control properties state by audio or the like. Such means for informing the control properties state by sound or the like are also controlled by the control circuit 32 and the like, as with the control properties state display unit 401.

According to the present embodiment described above, in addition to the advantages of the first through third embodiments, the current control properties state can be easily known. Thus, the state of the treating instrument and the organism tissue is notified to the operator, and in the event that an abnormal state occurs in either, this is notified as well, so operability improves.

A seventh embodiment of the present invention will be described with reference to FIGS. 18 through 20. Incidentally, the following description is mainly a description regarding the points which differ from the above first embodiment, so components that are the same as those in the first embodiment will be denoted by the same reference numerals and description thereof will be omitted.

With the present embodiment, the operating panel 12 for example is provided with a cord type selecting unit 501 for selecting the type of cord 26 for the high-frequency cauterization treating instrument 3a which is the bipolar treating instrument shown in FIG. 5, and a constant-voltage control unit 511 is provided instead of the constant-voltage control unit 53 shown in FIG. 7.

The cord type selecting unit 501 has cord type selecting switches 502 for selecting the type of the cord 26.

Instead of the target voltage value storing unit 71, the constant-voltage control unit 511 has multiple target voltage value storing units 512a, 512b, and 512c, for storing target voltage values for excision according to the type of cord 26, and also a cord selecting unit 514a for selecting one target voltage value from the target voltage values stored in the multiple target voltage value storing units 512a, 512b, and 512c, and providing this to the selecting unit 73, according to the settings of the cord type selecting unit 501. Also, instead of the target voltage value storing unit 72, the constant-voltage control unit 511 has multiple target voltage value storing units 513a, 513b, and 513c, for storing target values for coagulation according to the type of cord 26, and also a cord selecting unit 514b for selecting one target voltage value from the target voltage values stored in the multiple target voltage value storing units 513a, 513b, and 513c, and providing this to the selecting unit 73, according to the settings of the cord type selecting unit 501.

The operation of the present embodiment configured thus will now be described. Incidentally, with the present embodiment, the points differing from the first embodiment are described.

As shown in the equivalent circuit shown in FIG. 19, electrostatic capacity is distributed between the two lines of the cord 26 of the high-frequency cauterization treating instrument 3a which is a bipolar treating instrument. High-frequency current flows through this cord 26, so generally a great power loss occurs due to the electrostatic capacity between the lines.

Further, the great power loss occurring due to the electrostatic capacity between the lines causes the effective electric power value consumed by the active electrode 25 to be smaller than the output power which is output from the high-frequency cauterization power source device 4, as shown in FIG. 20. As shown in the Figure, this phenomena is markedly exhibited in the event that the organism tissue deteriorates and the load impedance increases. Also, difference in the type of the cord 26, such as difference in length and the like, causes difference in the degree of power loss.

Accordingly, a selection switch is selected according to the type of the cord 26 with the cord type selecting switches 502. Thus, the constant-voltage control unit 511 outputs a target voltage value according to the type of the cord 26. This target voltage value is set so as to reduce the power loss due to the type of the cord 26. Accordingly, even in the event that different cords 26 are used, the effective power consumed at the active electrode 25 is generally the same.

According to the present embodiment described above, in addition to the advantages of the first embodiment, the effective power consumed at the active electrode is generally the same even in the event that the type of cord for the high-frequency cauterization treating instrument is different. Accordingly, even in the event that the cord type differs, the voltage provided to the organism tissue is generally the same under the same load impedance state, so the operator can perform treatment without taking the difference of cord type into consideration. As a result, operability improves.

Incidentally, application of the cord type selecting unit 501 and constant-voltage control unit according to the present embodiment is not restricted to the first embodiment; rather, this may be applied to other embodiments as well.

Also, the object of selection of the cord type selecting unit 501 is not restricted to the type of cord 26 of the high-frequency cauterization treating instrument 3a which is a bipolar treating instrument; rather, the types of cords 22 and 24 of the high-frequency cauterization treating instrument 3 which is a monopolar treating instrument may be included, as well.

Further, the voltage values of-the target voltage value storing units 512a, 512b, 512c, 513a, 513b, and 513c, may be set by input means such as the parameter value input unit 301 shown in FIG. 16 in conjunction with the fourth embodiment.

An eighth embodiment of the present invention will be described with reference to FIG. 21. Incidentally, the following description is mainly a description regarding the points which differ from the above seventh embodiment, so components that are the same as those in the seventh embodiment will be denoted by the same reference numerals and description thereof will be omitted.

As shown in the Figure, the present embodiment is provided with a cord 551 instead of the cord 26 shown in FIG. 5. This cord 551 is configured having a line portion 552, an electrode-side contact portion 553 which is provided to one end of this line portion 552 and is detachably connected to the active electrode 25, and a terminal-side connecting portion 554 which is provided to the other end of this line portion 552 and is detachably connected to the output terminals 11a and 11b of the high-frequency cauterization power source device 4.

The terminal-side connecting portion 554 is configured having a conducting pin 554a for electrically connecting the high-frequency cauterization power source device 4 and the electrode-side contact portion 553 via the line portion 552 by means of being connected to the output terminals 11a and 11b of the high-frequency cauterization power source device 4, and an identification pin 555 for the high-frequency cauterization power source device 4 to identify the type of the cord 551 by means of being connected to the output terminals 11a and 11b of the high-frequency cauterization power source device 4. The identification pin 555 has a resistor 555a of a resistance according to the type of cord 551.

The high-frequency cauterization power source device 4 has, instead of the cord type selecting unit 501 shown in FIG. 18, an unshown cord type judging unit which measures the resistance value of the resistor 555a based on the output voltage value obtained from the output voltage measuring circuit 36 shown in FIG. 6 and the output current value obtained from the output current measuring circuit 37 and discerns the type of cord 551, and controls the selecting units 514a and 514b.

The operation of the present embodiment configured thus will now be described. Incidentally, with the present embodiment, the points differing from the seventh embodiment are described.

Prior to the operation, the identification pin 555 is connected to the output terminals 11a and 11b of the high-frequency cauterization power source device 4, and a weak current for example is output from the high-frequency cauterization power source device 4. The output voltage measuring circuit 36 and output current measuring circuit 37 measure the output voltage value and output current value corresponding to the resistance value of the resistor 555a of the identification pin 555, and provides the output voltage value and output current value to the cord type judging unit. The cord type judging unit calculates the resistance value of the resistor 555a from the provided output voltage value and output current value, and switches over the cord selecting unit 514a and voltage selecting unit 514b. Accordingly, the target voltage value corresponding to the type of the cord 551 is selected from the target voltage value storing units 512a, 512b, 512c, 513a, 513b, and 513c.

Next, the identification pin 555 of the cord 551 is removed from the output terminals 11a and 11b, and the conducting pin 554a is connected to the output terminals 11a and 11b, while the electrode-side contact portion 553 is connected to the active electrode 25. Then, the operation is started. Thus, power of a power value and voltage value wherein the difference in power value and voltage value due to difference in the type of the cord 551 has been reduced, is provided to the active electrode 25.

Incidentally, an arrangement may be made wherein, at the time of discerning the type of cord 551, the output voltage value or output current value output by the high-frequency cauterization power source device 4 is determined beforehand, so that the cord type discerning unit calculates the resistance value of the resistor 555a from one or the other of the measured output voltage value or output current value. In this case, an arrangement may be made wherein the cord type discerning unit does not calculate the resistance value of the resistor 555a, but discerns the type of the cord 551 from the output voltage value or output current value as corresponding to the resistance value of the resistor 555a.

Also, the electrode-side contact portion 553 is not restricted to being detachably connected to the active electrode 25, but rather may be integrally formed with the active electrode 25.

According to the present embodiment described above, in addition to the advantages of the seventh embodiment, the type of cord can be automatically discerned, thus improving operability.

A ninth embodiment of the present invention will be described with reference to FIG. 22. Incidentally, the following description is mainly a description regarding the points which differ from the above seventh embodiment, so components that are the same as those in the seventh embodiment will be denoted by the same reference numerals and description thereof will be omitted.

As shown in the Figure, with the present embodiment, a cord 571 is provided instead of the cord 26 of the high-frequency cauterization treating instrument 3a.

This cord 571 is configured having a terminal-side contact portion 571a on one end, detachably connected to the output terminals 11a and 11b of the high-frequency cauterization power source device 4, and an electrode-side connecting portion 571b on the other end, detachably connected to the active electrode 25.

Also, in addition to the first embodiment, the high-frequency cauterization power source device 4 comprises a terminal 581 to which the electrode-side connecting portion 571*b* is connectable, a reference resistor 582 connected to this terminal 581, a voltage measuring circuit 583 for measuring the voltage value on both sides of this reference resistor 582, a current measuring circuit 584 for measuring the electrical current value flowing through the reference resistor 582, and a cord type discerning unit 585 for calculating a power loss value for the cord 571 by calculating the difference between the output power value obtained from the output voltage value and output current value obtained from the output voltage measuring circuit 36 and output current measuring circuit 37, and the output power value obtained from the voltage value and current value obtained from the voltage-measuring circuit: 583 and current measuring circuit 584, discerning the type of the cord 571 from this power loss value, and controlling the selecting units 514*a* and 514*b* shown in FIG. 18.

The operation of the present embodiment configured thus will now be described. Incidentally, with the present embodiment, the points differing from the seventh embodiment are described.

Prior to the operation, the connecting portion 571*a* of the cord 571 is connected to the output terminals 11*a* and 11*b*, the electrode-side connecting portion 571*b* is connected to the terminal 581, and a weak current for example is output from the high-frequency cauterization power source device 4. Thus, an electric current flows through the cord 571 connected to the output terminals 11*a* and 11*b* and the reference resistor 582 connected via the terminal 581.

Now, the cord type discerning unit 585 calculates the output power value from the output voltage value measured by the output voltage measuring circuit 36 and output current value measured by the output current measuring circuit 37, and calculates the effective power value consumed by the reference resistor 582, based on the voltage value measured at the voltage measuring circuit 583 and the current value measured at the current measuring circuit 584. Then, the power loss value of the cord 571 is calculated by obtaining the difference between the output power value and effective power value, thereby discerning the type of the cord 571 from this power loss value, causing switching action of the selecting units 514*a* and 514*b* according to these judging results. Accordingly, the target voltage value corresponding to the type of the cord 571 is selected from the target voltage value storing units 512*a*, 512*b*, 512*c*, 513*a*, 513*b*, and 513*c*, shown in FIG. 18.

Next, the electrode-side connecting portion 571*b* is removed from the terminal 581, this electrode-side connecting portion 571*b* is connected to the active electrode 25, and the operation is started. Thus, power of a power value and voltage value wherein the difference in power value and voltage value due to difference in the type of the cord 571 has been reduced, is provided to the active electrode 25.

Also, the resistance value of the reference resistor 582 is preferably appropriate for calculating the power loss value of the cord 571, and may be around 1 kΩ, for example.

According to the present embodiment described above, in addition to the advantages of the seventh embodiment, the type of cord can be automatically discerned, thus improving operability.

A tenth embodiment of the present invention will be described with reference to FIGS. 23 through 25. Incidentally, the following description is mainly a description regarding the points which differ from the above first embodiment, so components that are the same as those in the first embodiment will be denoted by the same reference numerals and description thereof will be omitted.

With the present embodiment, the configuration of the operating panel 12 shown in FIG. 23 and the configuration of the control circuit 632 shown in FIG. 24 differ from those in the first embodiment.

As shown in FIG. 23, the operating panel 12 is comprised having a display portion 601 inscribed with the name of the type of electrode form of the electrode portion 21*a* of the active electrode 21 connectable to the high-frequency cauterization treating instrument 3, and a treating instrument selecting switch 602 for selecting the high-frequency cauterization treating instrument 3 which has the electrode form of the electrode portion 21*a* inscribed on the display portion 601.

In the Figure, selection can be made of one of the electrode forms "loop electrode", "band electrode", and "roller electrode".

Incidentally, the display portion 601 may describe not only the electrode form, but may display shapes or symbols indicating the type of electrode portion 21*a*, or may display other matters such as names or symbols indicating the type of high-frequency cauterization treating instrument 3. Also, the treating instrument selecting switch 602 is not restricted to the rotating switch such as shown in the Figure, and may be push-button switcher or other types of switches. Further, lamps 603 for notifying the electrode form and the like that is currently selected by be provided in the vicinity of the display portion 601.

As shown in FIG. 24, the control circuit 632 comprises a waveform control unit 51, a load impedance calculating unit 642, an output power calculating unit 643, a constant-voltage control unit 644, a constant-power control unit 645, a constant-current control unit 646, and a control properties selecting unit 647.

The load impedance calculating unit 642 inputs the output voltage value signals and the output current value signals obtained from the output voltage measuring circuit 36 and output current measuring circuit 37 via the A/D conversion circuits 36*a* and 37*a*, and calculates load impedance. The output power calculating unit 643 inputs the output voltage value signals and the output current value signals obtained from the output voltage measuring circuit 36 and output current measuring circuit 37 via the A/D conversion circuits 36*a* and 37*a*, and calculates output power. The constant-voltage control unit 644 inputs the output voltage value signals obtained from the output voltage measuring circuit 36 via the A/D conversion circuit 36*a*, and obtains amplification rate signals for controlling the variable amplifying circuit 34 such that the output voltage from the high-frequency cauterization power source device 4 is maintained at a constant. The constant-power control unit 645 inputs the output power value signals obtained by the output power calculating unit 643, and obtains amplification rate signals for controlling the variable amplifying circuit 34 such that the output power from the high-frequency cauterization power source device 4 is maintained at a constant. The constant-current control unit 646 inputs the output current value signals obtained from the output current measuring circuit 37 via the A/D conversion circuit 37*a*, and obtains amplification rate signals for controlling the variable amplifying circuit 34 such that the output current from the high-frequency cauterization power source device 4 is maintained at a constant. The control properties selecting unit 647 inputs the load impedance signals obtained by the load impedance calculating unit 642, and according to the range of the load impedance, selectively allows passage of one of the following; the amplification rate signals obtained by the constant-voltage control unit 644, the amplification rate signals obtained by the constant-power control unit 645, and the amplification rate signals obtained by the constant-current control unit 646; following which the amplification rate signals allowed passage are provided to the variable amplifying circuit 34 via the D/A conversion circuit 34a.

The load impedance calculating unit 642 calculates the load impedance by performing division of the output voltage value signals and the output current value signals, for example.

The output power calculating unit 643 calculates output power by multiplying the output voltage value signals and the output current value signals, for example.

The constant-voltage control unit 644 is configured having a target voltage value storing unit 644a for storing a target 5voltage value to maintain constant, a voltage value comparing unit 644b for detecting the difference between this target voltage value and the output voltage value, and an amplification rate rheostat unit 644c for increasing or decreasing the amplification rate to be provided to the variable amplifying circuit 34, according to the output of the voltage value comparing unit 644b.

The constant-power control unit 645 is configured having a target power value storing unit 645a for storing a target power value to maintain constant, a power value comparing unit 645b for detecting the difference between this target power value and the output voltage value obtained from the output power calculating unit, and an amplification rate rheostat unit 645c for increasing or decreasing the amplification rate to be provided to the variable amplifying circuit 34, according to the output of the power value comparing unit 645b.

The constant-current control unit 646 is configured having for example three target current value storing units 651a, 651b, and 651c, for storing target current values to be maintained at a constant corresponding to multiple types of electrode forms, a target current value selecting unit 652 for allowing passage of one of the storing target current value signals of the target current value storing units 651a, 651b, and 651c according to the setting state of the treating instrument selecting switch 602, a current value comparing unit 653 for detecting the difference between this target current value obtained by passage through the target current value selecting unit 652 and the output current value, and an amplification rate rheostat unit 654 for increasing or decreasing the amplification rate to be provided to the variable amplifying circuit 34, according to the output of the current value comparing unit 653.

The control properties selecting unit 647 is configured such that for example, in the event that the value of load impedance obtained from the load impedance calculating unit 642 is contained within a predetermined range from the rated load impedance, the amplification rate signal obtained from the constant-power control unit 645 is allowed passage, in the event that the value of load impedance is smaller than the predetermined range from the rated load impedance, the amplification rate signal obtained from the constant-current control unit 646 is allowed passage, and in the event that the value of load impedance is greater than the predetermined range, the amplification rate signal obtained from the constant-voltage control unit 644 is allowed passage.

The operation of the present embodiment configured thus will now be described.

First, at the time of using the electric surgical operation apparatus 1, the cables 22 and 24 of the high-frequency cauterization treating instrument 3 are connected to the output terminals 11a and 11b of the high-frequency cauterization power source device 4, the type of high-frequency cauterization treating instrument 3 connected thereof is selected by the treating instrument selecting switch 602, and the feedback electrode portion 23 is brought into plane contact with body surface 2b other than the area 2a to be treated, of the patient 2.

Now, due to the type of the high-frequency cauterization treating instrument 3 being selected with the treating instrument selecting switch 602, the target current value selecting unit 652 allows passage of, out of the storing target current value signals of the target current value storing units 651a, 651b, and 651c respectively corresponding to the multiple types of the high-frequency cauterization treating instruments 3, the target current value corresponding to the type of the one of the multiple high-frequency cauterization treating instruments 3 connected, and this target current value is allowed passage and is provided to the current value comparing unit 653.

Next, in order to perform excision or coagulation of the patient at the area 2a to be treated, the electrode portion 21a of the active electrode 21 is brought into contact with the area 2a to be treated, and the excision switch 5a or coagulation switch 5b of the foot switch 5 is operated.

With the waveform control unit 51 of the control circuit 632, control signals are provided to the waveform generating circuit 33 so as to cause output of excision or coagulation high-freqeuncy waveforms. The waveform generating circuit 33 then generates excision or coagulation high-freqeuncy waveforms, according to the provided control signals. The high-frequency waves are amplified at the variable amplifying circuit 34, boosted at the booster circuit 35, and provided to the high-frequency cauterization treating instrument 3 via the output terminals 11a and 11b.

Consequently, a high-frequency current is provided to the electrode portion 21a in contact with the area 2a to be treated, and the area 2a to be treated is heated by the high-frequency current. Further, the area 2a to be treated is heated by the electrode portion 21a heated by the high-frequency current. The current from the electrode portion 21a of the active electrode 21 concentratedly flows into the area 2a to be treated.

The current that has flown in to the area 2a to be treated is dispersed and recovered by the feedback electrode portion 23 which is in plane contact with body surface 2b other than the area 2a to be treated, so energy provided to the organism tissue at portions other than the area 2a to be treated is suppressed. Also, the feedback electrode portion 23 is formed greater than the electrode portion 21a of the active electrode 21, so heating of the feedback electrode portion 23 is suppressed.

At the time that providing of the high-frequency current to the high-frequency cauterization treating instrument 3 begins, the load impedance of the organism tissue at the area 2a to be treated is low, and excision or coagulation operations do not occur until the load impedance at the area 2a to be treated, being heated, reaches a predetermined level.

Once the high-frequency current is output from the high-frequency cauterization power source device 4, the output voltage and output current of the high-frequency waves are measured by the output voltage measuring circuit 36 and output current measuring circuit 37. Then, the output voltage value signals and output current value signals obtained by the output voltage measuring circuit 36 and output current measuring circuit 37 are provided to the control circuit 632 via the respective A/D conversion circuits 36a and 37a.

The constant-voltage control unit 644 compares the provided output voltage value with the target voltage value, and outputs an amplification rate signal increased or decreased such that the output voltage value can be maintained at the target voltage value. On the other hand, the output power calculating unit 643 calculates and outputs the output power value from the provided output voltage value and output current value. The constant-power control unit 645 compares this output power value with the target bower value, and outputs an amplification rate signal increased or decreased such that the output power value can be maintained at the target power value. Also, the constant-current control unit 646 compares the provided output current value with the target current value, and outputs an amplification rate signal increased or decreased such that the output current value can be maintained at the target current value. Further, the load impedance calculating unit 642 calculates the load impedance from the provided output voltage value signals and output current value signals, and controls the control properties selecting unit 647 according to the range of the load impedance.

Now, in the event that the load impedance is smaller than the predetermined range, the control properties selecting unit 647 allows passage of the amplification rate signals obtained from the constant-current control unit 646. The amplification rate signals are provided to the variable amplifying circuit 34 via the D/A conversion circuit 34*a*, and the variable amplifying circuit 34 adjusts the amplification rate of the high-frequency waves according to the provided amplification rate signals.

That is, as shown in FIG. 25, in the event that the load impedance is smaller than the predetermined range, the output high-frequency waves are subjected to constant-current control. Now, the properties curves and in the constant-current control region in the Figure represent the difference in properties according to the target current value selected with the treating instrument selecting switch 602 according to the type of high-frequency cauterization treating instrument 3.

That is to say, in the event that the electrode portion 21*a* of the high-frequency cauterization treating instrument 3 is a small electrode portion 21*a* such as with a loop electrode, the current density flowing through the electrode portion 21*a* is great, and heating of the electrode portion 21*a* is fast, so a small target current value is selected, and so the properties of the control properties curves in the Figure are obtained, for example.

Also, in the event that the electrode portion 21*a* is a large electrode portion 21*a* such as with a roller electrode, the current density flowing through the electrode portion 21*a* is small, and heating of the electrode portion 21*a* is slow, so a large target current value is selected, and so the control properties of the properties curves in the Figure are obtained, for example.

Thus, the difference in the heating amount of the area 2*a* to be treated owing to the difference in the type of the electrode portion 21*a* of the high-frequency cauterization treating instrument 3 is reduced, and the difference in speed of increasing load impedance at the area 2*a* to be treated is reduced.

The load impedance of the organism tissue of the heated area 2*a* to be treated increases once the moisture is reduced and deterioration progresses, and the load impedance reaches a value in a predetermined range from the rated load impedance. At this point, the output voltage increases, and the excision or coagulation operation is started on the area 2*a* to be treated.

Then, once the load impedance value reaches the predetermined range, the control properties selecting unit 647 which has obtained the load impedance value calculated at the load impedance calculating unit 642 allows passage of the amplification rate signals obtained from the constant-power control unit 645, which are provided to the variable amplifying circuit 34 via the D/A conversion circuit 34*a*. That is to say, as shown in FIG. 25, in the event that the load impedance is in the predetermined range, the output high-frequency waves are subjected to constant-power control.

Also, in the event that the load impedance becomes greater than the predetermined range, the control properties selecting unit 647 which has obtained the load impedance value calculated at the load impedance calculating unit 642 allows passage of the amplification rate signals obtained from the constant-voltage control unit 644, which are provided to the variable amplifying circuit 34 via the D/A conversion circuit 34*a*. That is, as shown in FIG. 25, in the event that the load impedance is greater than the predetermined range, the output high-frequency waves are subjected to constant-voltage control.

In this way, according to the present embodiment, in the event that the load impedance of the area to be treated is smaller than a predetermined range, the output high-frequency waves are subjected to constant-current control, and at this time, the output high-frequency waves are subjected to constant-current control so as to maintain different target current values according to difference in the form or the like of the electrode portion of the active electrode of the high-frequency cauterization treating instrument. Accordingly, advantages can be obtained such as the difference in delay time from operating the foot switch till starting excision or coagulation being reduced, unnaturalness in the operation sense due to this delay time being done away with, and operability increasing.

Also, in the event that the load impedance of the area to be treated is in the predetermined range wherein excision or coagulation can be performed on the area to be treated, the output high-frequency waves are subjected to constant-power control. Accordingly, advantages can be obtained such as the output high-frequency energy provided to the area to be treated for excision or coagulation being stabilized, and arc discharge being generated in a stable manner.

Further, in the event that the load impedance of the area to be treated is greater than the predetermined range, the output high-frequency waves are subjected to constant-voltage control. Accordingly, advantages can be obtained such as the output voltage being kept from becoming too great, and operability increasing.

Incidentally, the selection items to be selected with the treating instrument selecting switch 602 are not restricted to information indicating the type of electrode form; rather, this may be information indicating the size or volume of the electrode, information indicating the material of the electrode. At this time, generally, the information of the size, volume, or material of the electrode correlates with the delay time from starting heating to starting excision or coagulation, and the target current value may be selected from this information. For example, in the event that the same voltage is used, the delay time can be adjusted by changing the target current value. Thus, the time till excision or coagulation can be selected or changed according to the experience or skill of the technician.

Also, the selection items to be selected with the treating instrument selecting switch 602 may be information corresponding with names by which the type of electrode can be identified, such as electrode model Nos., allowing information such as the form, size, volume, material, etc., of the electrode to be determined.

Also, in addition to control of the high-frequency waveform according to operation of the excision switch 5a or the coagulation switch 5b of the foot switch 5, i.e., according to the excision and coagulation operations, control of electric current value may be performed, as well.

An eleventh embodiment of the present invention will be described with reference to FIG. 26. Incidentally, the following description is mainly a description regarding the points which differ from the above tenth embodiment, so components that are the same as those in the tenth embodiment will be denoted by the same reference numerals and description thereof will be omitted.

As shown in the Figure, with the control circuit 732 according to the present embodiment, a microprocessor 32a comprises a waveform control unit 51, an amplification rate rheostat unit 644c, an amplification rate rheostat unit 645c, an amplification rate rheostat unit 654c, and a control properties selecting unit 647.

The load impedance calculating unit 642 is configured of a load impedance measuring circuit 701 which is a hardware circuit having the same role. Also, the output power calculating unit 643 is configured of a output power calculating circuit 702 which is a hardware circuit having the same role. Also, the voltage value comparing unit 644b is configured of a voltage value comparing circuit 712 which is a hardware circuit having the same role. Also, the target voltage value storing unit 644a is configured of a trimmer 711 which is a hardware circuit having the same role. Also, the power value comparing unit 645b is configured of a power value comparing circuit 722 which is a hardware circuit having the same role. Also, the power value storing unit 645a is configured of a trimmer 721 which is a hardware circuit having the same role. Also, the current value comparing unit 653 is configured of a current value comparing circuit 733 which is a hardware circuit having the same role. Also, the target current value storing units 651a, 651b, and 651c, are configured of trimmers 731a, 731b, and 731c, which are hardware circuits having the same role. Also, the target current value selecting unit 652 is configured of a target current value selecting circuit 732 which is a hardware circuit having the same role.

Incidentally, the A/D conversion circuit is deleted as appropriate from the output of the hardware circuits regarding which output signals are not provided to the microprocessor 32a and the A/D conversion circuit is inserted as appropriate to the output of the hardware circuits regarding which output signals are directly provided to the microprocessor 32a.

Further, it is needless to say that the output signals of the output voltage measuring circuit 36, output current measuring circuit 37, load impedance measuring circuit 701, output power calculating circuit 702, trimmer 711, voltage value comparing circuit 712, trimmer 721, power value comparing circuit 722, trimmers 731a, 731b, and 731c, and current value comparing circuit 733, may be signals of voltage corresponding to the output values of each circuit.

Incorporating the control circuit 732 of the configuration according to the present embodiment is advantageous in that the processing of the control circuit can be speeded up as compared with an arrangement wherein all functions making up the control circuit are assembled as microprocessor.

A twelfth embodiment of the present invention will be described with reference to FIGS. 27 and 28. Incidentally, the following description is mainly a description regarding the points which differ from the above tenth embodiment, so components that are the same as those in the tenth embodiment will be denoted by the same reference numerals and description thereof will be omitted.

As shown in FIG. 27, with the operating panel 12 according to the present embodiment, in addition to the selection items indicating the type of high-frequency cauterization treating instrument 3 such as electrode form or the like making up the display unit 601 indicating the selection items to be selected by the treating instrument selection switch 602, a selection item 801 inscribed with "automatic electrode selection" is provided, for automatically recognizing the type of the high-frequency cauterization treating instrument 3 such as electrode form or the like, and selecting the operating mode.

Then, as shown in FIG. 28, with the present embodiment, a control circuit 811 is provided instead of the control circuit <632 of the tenth embodiment. With this control circuit 811, a treating instrument automatic selection unit 821 is inserted partway through the signals provided to the constant-current control unit 646 from the treating instrument selection switch 602.

The treating instrument automatic selection unit 821 is configured having a load impedance storing unit 831 for storing the load impedance calculated by the load impedance calculating unit 642 at the timing of the foot switch 5 being operated for example, an impedance comparing unit 832 for comparing the load impedance value stored in the load impedance storing unit 831 with the impedance values obtained by short-circuiting the electrode of each of the high-frequency cauterization treating instruments 3 with the feedback electrode portion 23 and obtaining a treating instrument selection signal for selecting the high-frequency cauterization treating instrument 3 with the closest impedance for example, and a treating instrument selection signal selecting unit 833 for selectively allowing passage of the treating instrument selection signal from the treating instrument selection switch 602 and the treating instrument selection signal obtained by the impedance comparing unit 832, and providing this to the constant-current control unit 646.

In the event that the selection item 801 is selected by the treating instrument selection switch 602, the treating instrument selection signal selecting unit 833 allows passage of the treating instrument selection signals obtained by the impedance comparing unit 832. In the event that an item other than the selection item 801 is selected by the treating instrument selection switch 602, passage is allowed for treating instrument selection signals.

The operation of the present embodiment configured thus will now be described. Incidentally, with the present embodiment, the points differing from the tenth embodiment are mainly described.

Prior to the operation, the selection item 801 is selected with the treating instrument selection switch 602, while the electrode portion 21a of the active electrode 21 of the high-frequency cauterization treating instrument 3 is brought into contact at a predetermined position on the feedback electrode portion 23, and the excision switch 5a of the foot switch 5 for example is operated.

This operation of the excision switch 5a causes high-frequency current to be output from the high-frequency cauterization power source device 4 to the high-frequency cauterization treating instrument 3, the impedance of the short-circuited high-frequency cauterization treating instrument 3 is calculated by the load impedance calculating unit 642, and stored in the impedance storing unit 831.

At this time, in the event that the electrode form of the electrode portion 21a is small, for example in the case of a loop electrode, a small impedance value is calculated, and in the event that the electrode form thereof is large, for example in the case of a roller electrode, a large impedance value is calculated.

Then, a treating instrument selection signal for selecting the high-frequency cauterization treating instrument 3 with a short-circuited impedance value closest for example to the short-circuited impedance stored in the impedance storing unit 831 is obtained from the impedance comparing unit 832. This treating instrument selection signal passes through the treating instrument selection signal selecting unit 833 and is provided to the target current value selecting unit 652. Other operations are the same as the tenth embodiment. The operations in the event that an item other than the selection item 801 is selected with the treating instrument selection switch 602 are the same as those of the tenth embodiment.

Incidentally, in order to facilitate ease of obtaining the short-circuited impedance of the high-frequency cauterization treating instrument 3 with the load impedance calculating unit 642 or the like, the feedback electrode portion 23 may be formed of a high-impedance electroconductive rubber, for example. Also, in order to prevent overcurrent in the case of selecting the selection item 801 with the treating instrument selection switch 602, the output voltage may be controlled so as to be smaller than normal.

According to the present embodiment described above, in addition to the advantages of the tenth embodiment, the type of high-frequency cauterization treating instrument 3 can be automatically detected. Accordingly, in the event that there are a great number of high-frequency cauterization treating instruments to select from, the load on the technician to select the type of high-frequency cauterization treating instrument is relieved, thus improving operability.

A thirteenth embodiment of the present invention will be described with reference to FIGS. 29 through 37. Incidentally, the following description is mainly a description regarding the points which differ from the above first embodiment, so components that are the same as those in the first embodiment will be denoted by the same reference numerals and description thereof will be omitted.

As shown in FIG. 29, in addition to the configuration of the high-frequency cauterization power source device 4 described with the first embodiment, the present embodiment further comprises a buzzer 938 which sounds, being controlled by the control circuit 32.

Also, as shown in FIG. 30, the operating panel 900 is provided with a withstanding voltage value input unit 941 for inputting the withstanding voltage value with is the maximum voltage value which can be applied to the high-frequency cauterization treating instrument 3. This withstanding voltage value input unit 941 is configured having a display portion 942 which displays the current setting value for the withstanding voltage value, and buttons 943 and 944 for increasing or decreasing the set withstanding voltage value by depressing, for example.

Along with the buzzer 938, providing the operating panel 900 with the withstanding voltage value input unit 941 causes the control circuit 932 to be configured having a waveform control unit 51, an output control unit 952, a withstanding voltage value correction unit 953, an output voltage restricting control unit 954, a load impedance measuring unit 955, a first insulation destruction judging unit 956, a second insulation destruction judging unit 957, a third insulation destruction judging unit 958, and an output suppression control unit 959, as shown in FIG. 31.

The output control unit 952 outputs the gain value to be provided to the variable amplifying circuit 34 according to the output power level and the like set at the operating panel 12. The withstanding voltage value correction unit 953 corrects the withstanding voltage value input by the withstanding voltage value input unit 941 so that there is leeway in the withstanding voltage value. The output voltage restricting control unit 954 increases or decreases the gain value output from the output control unit 952 so that the output voltage value of the high-frequency power output from the high-frequency cauterization power source device 4 does not exceed the withstanding voltage value corrected by the withstanding voltage value correction unit 953. The load impedance measuring unit 955 takes the output voltage value and the output current value obtained from the output voltage measuring circuit 36 and output current measuring circuit 37 via the A/D conversion circuits 36a and 37a and subjects these to division for example, thereby calculating load impedance value. The first insulation destruction judging unit 956, second insulation destruction judging unit 957, and third insulation destruction judging unit 958 monitor the state of the load impedance value obtained by the load impedance measuring unit 955, and makes judgment regarding whether or not insulation destruction has occurred at the high-frequency cauterization treating instrument 3. The output suppression control unit 959 controls the gain value so as to suppress output of high-frequency power from the high-frequency cauterization power source device 4 to the high-frequency cauterization treating instrument 3 in the event that at least one of the insulation destruction judging units 957 of 958 detects insulation destruction at the high-frequency cauterization treating instrument 3.

The output voltage restricting control unit 954 is configured having a voltage comparing unit 954a for comparing the output voltage value provided from the output voltage measuring circuit 36 via the A/D conversion circuit 36a with the withstanding voltage value corrected by the withstanding voltage value correction unit 953, and a gain value rheostat unit 954b for increasing or decreasing the gain value so that the output voltage value does not exceed the corrected withstanding voltage value, according to the comparison results of this voltage comparing unit 954a.

The first insulation destruction judging unit 956 is arranged so as to drive the buzzer 938 in the event that detection is made of the danger of insulation destruction at the high-frequency cauterization treating instrument 3, in order to audibly inform the technician of this state. Also, an unshown warning display is displayed on the operating panel 12, in order to visually inform the technician of this state.

In the event that at least one of the second insulation destruction judging unit 957 and third insulation destruction judging unit 958 detect occurrence of insulation destruction at the high-frequency cauterization treating instrument 3, the output power is suppressed with the output suppression control unit 959. The buzzer 938 is driven in order to audibly inform the technician of occurrence of insulation destruction. Also, a warning is displayed in order to visually inform the technician of the occurrence of insulation destruction.

Also, the buzzer 938 and warning display differ in the tone of the buzzer 938 and the contents of the warning display, depending on whether these are driven by the insulation destruction judging unit 956 or driven by the other insulation destruction judging units 957 and 958.

The gain value output from the output control unit 952 is not restricted to output of gain value according to the set output power level, but may have constant-voltage control functions for increasing or decreasing the gain value for maintaining the output voltage value provided from the output voltage measuring circuit 36 via the A/D conversion circuit 36a so as to maintain the same to a predetermined voltage value. Also, this may have constant-current control functions for increasing or decreasing the gain value for maintaining the output current value provided from the output current measuring circuit 37 via the A/D conversion circuit 37a so as to maintain the same to a predetermined current value. Further, constant-power control functions may be provided, wherein an output power value is obtained from the output voltage value and output current value and the gain value is increased or decreased so as to maintain this output power value at a constant power value.

This output suppression control unit 959 may suppress the output power by stopping the output power, or by reducing the output power level to a weak level. Also, the output suppression control unit 959 may suppress the output power by increasing or decreasing the gain value provided to the variable amplifying circuit 34, or may suppress the output power by providing signals other than signals indicating gain values to the waveform generating circuit 33 or the variable amplifying circuit.

As shown in FIG. 32, the first insulation destruction judging unit 956 is comprised having a determining value storing unit 56a storing a predetermined determining value, and an impedance value comparing unit 956b for comparing the determination value of this determining value storing unit 956a and the load impedance value, and judging that there is a good change that insulation destruction has occurred in the event that the load impedance value is smaller than the judging value.

Here, the judging value may be 1,000 Ω, a figure obtained by experience. Incidentally, what is required of the configuration of the insulation destruction judging unit 956 is a configuration which judges that there is a good change that insulation destruction has occurred in the event that the load impedance value is smaller than a certain judging value, so the configuration shown in the Figure is not necessarily required.

As shown in FIG. 33, the second insulation destruction judging unit 957 is configured having for example, a rate-of-change calculating unit 957a for obtaining the rate of change of the load impedance as to time, an increase determining unit 957b for detecting a state of increase of the load impedance value by the output of this rate-of-change calculating unit 957a, and a reduction determining unit 957c for judging that insulation destruction has occurred in the event that load impedance rapidly drops at a time that the load impedance has been increasing, from the output of the rate-of-change calculating unit 957a and increase determining unit 957b.

Incidentally, the insulation destruction judging unit only needs to be configured so as to judge that insulation destruction has occurred in the event that load impedance rapidly drops at a time that the load impedance has been increasing, so the configuration shown in the Figure is not necessarily required.

As shown in FIG. 34, the third insulation destruction judging unit 958 has a change amount calculating unit 958a for calculating the amount of change of the load impedance value for example, and detecting a low change amount state wherein the amount of change is little, and a timer unit 958b for judging that insulation destruction has occurred in the event that the low change amount state detected by the change amount calculating unit 958a continues and exceeds a predetermined amount of time.

Here, the predetermined amount of time may be 5 seconds, for experience. Now, the insulation destruction judging unit 958 only needs to be configured so as to judge that insulation destruction has occurred in the event that the low change amount state of the load impedance value continues and exceeds a predetermined amount of time, so the configuration shown in the Figure is not necessarily required.

The operation for preventing insulation destruction according to the present embodiment configured as described above will be described.

The withstanding voltage value input before the treatment from the withstanding voltage value input unit 941 is subjected to correction by subtracting 10% for example from the set withstanding voltage value by the withstanding voltage value correcting unit 953 so as to have leeway, and the corrected withstanding voltage value is provided to the output voltage restricting control unit 954. On the other hand, the output voltage value is measured by the output voltage measuring circuit 36 via the A/D conversion circuit 36a, and is provided to the output voltage restricting control unit 954 and is monitored.

That is, in the event that 100 V withstanding voltage value is set at the withstanding voltage value input unit 941, correction is made by subtracting 10% for example from the set withstanding voltage by the withstanding voltage correcting unit 953, and the corrected withstanding voltage value of 90 V is provided to the output voltage restricting control unit 954.

Now, in the event that the output voltage value rises due to the load impedance increasing, of the output power value becomes too great due to the output voltage level having been set too great, such the that output voltage value exceeds the corrected withstanding voltage value, the voltage value comparing unit 954a of the output voltage restricting control unit 954 detects this state. Then, the gain value rheostat unit 954b increases or decreases the gain value such that the output voltage value does not exceed the corrected withstanding voltage value. Accordingly, the output voltage value does not exceed the corrected withstanding voltage value, so insulation destruction of the high-frequency cauterization treating instrument 3 can be prevented.

Also, even in case with differing output power level settings, the output control value is controlled to the predetermined correction withstanding voltage value, so while voltage restricting control is being performed, the output properties are generally the same, regardless of the settings of the output power level, as shown in FIG. 9.

Next, the operation in the event that insulation destruction has occurred, will be described.

As shown in FIG. 35, an electroconducting material such as a conducting line 21b is inserted through the active electrode 21 for providing high-frequency current to the electrode unit 21a. Insulating material such as an insulating covering 21c is provided to portions other than the electrode portion 21a of the active electrode 21.

With the electric surgical operation apparatus 1 according to the present embodiment, measures are taken as described above in order to prevent insulation destruction of the insulating covering 21c, by controlling such that the output voltage does not exceed the withstanding voltage value of the high-frequency cauterization treating instrument 3, but there is a chance that insulation destruction may occur due to external heat, shock, or chemical reactions, damaging the insulating covering 21c, and exposing the conducting line 21b.

In the event that this insulation destruction occurs and the insulation destruction portion comes into contact with the organism tissue for example, electric current leaks from this contact portion 2c. The electric surgical operation apparatus 1 according to the present embodiment has the following means of avoiding trouble originating from insulation destruction.

First, the operation of the first insulation destruction judging unit 956 which is a means for avoiding trouble originating from insulation destruction, will be described.

In the event that neither the electrode portion 21a nor the active electrode 21 are in contact with the organism tissue, there is no output current. Accordingly, the load impedance value obtained at the load impedance measuring unit 955 is great. At this time, the first insulation destruction judging unit 956 drives neither the buzzer 938 nor the warning display.

In the event that the electrode portion 21a is placed in contact with the area 2a to be treated for treatment thereof, output current occurs, so as a matter of course, load impedance decreases as compared to the case of no contact. The first insulation destruction judging unit 956 which has detected this state drives the buzzer 938 and the warning display. At this time, the technician judges that the buzzer 938 and the warning display have been generated not due to insulation destruction, but due to the electrode portion 21a being placed in contact with the area 2a to be treated for the first time.

On the other hand, in the event that the technician brings the electrode portion 21a near to the area 2a to be treated but maintains non-contact, and the above insulation destruction portion comes into contact with the organism tissue, electric current flows from the insulation destruction portion into the organism tissue. In this case, the first insulation destruction judging unit 956 detects a reduction in load impedance as compared to the state of non-contact, and drives the buzzer 938 and the warning display. At this time, the technician can judge that the buzzer 938 and the warning display have been generated even though the electrode portion 21a has not been brought into contact with the area 2a to be treated, so insulation destruction has occurred. Then, the technician, upon confirming the insulation destruction having occurred, takes steps such as aborting the treatment, thereby avoiding trouble occurring due to the insulation destruction.

Incidentally, the first insulation destruction judging unit 956 drives the buzzer 938 and the warning display even in normal states wherein insulation destruction has not occurred. Accordingly, the tone and warning display contents of the buzzer 938 and the warning display differ from the buzzer 938 and the warning display driven by the insulation destruction judging units 957 and 958, telling the technician that this is a different case.

Next, the operation relating to the second insulation destruction judging unit 957 will be described.

Placing the electrode portion 21a in contact with the area 2a to be treated and continuing the electric current flow therefrom causes deterioration of the organism tissue, and the load impedance rises. In the event that the above insulation destruction portion comes into contact with the organism tissue, electric current leaks from the insulation destruction portion into the this contact area 2c, and the load impedance as viewed from the high-frequency cauterization power source device 4 rapidly drops, as shown in FIG. 36.

The second insulation destruction judging unit 957 detects that the load impedance has rapidly dropped during rising of the load impedance, and judges that insulation destruction has occurred, drives the buzzer 938 and the warning display, and thus notifies the technician of the insulation destruction. Also, the output suppression control unit 959 controls the variable amplifying circuit 34 such that the output power is stopped or controlled to a weak level. Thus, the technician recognizes the occurrence of insulation destruction, and trouble owing to the insulation destruction is avoided.

Next, the operation relating to the third insulation destruction judging unit 958 will be described.

In the event that the insulation destruction portion comes into contact with the organism tissue at a place other than the area 2a to be treated, electric current leaks from the insulation destruction portion to this contact portion 2c, and progression of tissue deterioration at the area 2a to be treated with which the electrode portion 21a is in contact stops. In this state, a low change amount state wherein there is little amount of change in the load impedance occurs, as shown in FIG. 37.

In the event that the third insulation destruction judging unit 958 detects that this low change amount state continues for a predetermined amount of time, 5 seconds for example, judgment is made that insulation destruction has occurred, the buzzer 938 and the warning display are driven, and thus the technician is notified of the insulation destruction. Also, the output suppression control unit 959 controls the variable amplifying circuit 34 such that the output power is stopped or controlled to a weak level. Thus, the technician recognizes the occurrence of insulation destruction, and trouble owing to the insulation destruction is avoided.

As described above, according to the present embodiment, application of voltage exceeding the withstanding voltage value to the treating instrument can be prevented even without using special treating instruments, and insulation destruction of the treating instrument can be prevented.

Also, providing the insulation destruction judging unit and the like allows insulation destruction of the treating instrument to be detected in the event that insulation destruction of the treating instrument occurs, and trouble owing to insulation destruction of the treating instrument to be prevented.

Also, providing the insulation destruction judging unit and the like allows any danger of insulation destruction of the treating instrument to be detected, so avoidance of trouble owing to insulation destruction of the treating instrument is supported.

It is clearly understood that, with the present invention, a wide range of varying embodiments can be configured based on the present invention without departing from the spirit and scope thereof. The present invention is by no means limited by any such embodiments, except as restricted in the appended Claims.

What is claimed is:

1. An electric surgical operation apparatus, comprising:
  an active electrode which performs medical treatment to an area to be treated by applying electric energy to said area;
  an electric power supplying unit which supplies electric power to said active electrode;
  a measuring unit which measures at least one of an output voltage value and an output current value supplied to said active electrode from said electric power supplying unit;
  a discerning unit that discerns a condition of said area that is being treated based on one of said output voltage value and said output current value; and a voltage control unit that maintains said supplied electric power at a constant voltage after said discerning unit indicates that said area that is being treated has reached a predetermined condition.

2. An electric surgical operation apparatus according to claim 1, further comprising an input unit for setting the electric power output from said electric power supplying unit to an arbitrary value.

3. An electric surgical operation apparatus according to claim 1, wherein said discerning unit further outputs said condition of said area that is being treated.

4. An electric surgical operation apparatus according to claim 1, further comprising an input unit for instructing the type of medical treatment;
   wherein said electric power supplying unit further generates electric power of a waveform corresponding to the type of medical treatment selected by said input unit.

5. An electric surgical operation apparatus according to claim 1, further comprising a supplying path for supplying electric power to said active electrode, and a voltage value selecting unit for selecting a target voltage according to an electrostatic capacity of said supplying path.

6. An electric surgical operation apparatus according to claim 1, further comprising:
   a constant-current control unit for maintaining the current applied by said electric power supplying unit to said active electrode at a provided target current value; and
   a target current value selecting unit which is connected to said electric power supplying unit, for selecting said target current value according to the type of said active electrode.

7. An electric surgical operation apparatus according to claim 6, further comprising an input unit for instructing the type of medical treatment.

8. An electric surgical operation apparatus according to claim 6, further comprising a current value setting unit wherein current values according to the type of said active electrodes are set beforehand;
   wherein said target current value selecting unit selects a current value corresponding to the type of said active electrode, from the current values set in said current value setting unit.

9. An electric surgical operation apparatus according to claim 7, wherein said input unit further comprises an electrode type instructing unit for instructing the type of said active electrode to said target current value selecting unit.

10. An electric surgical operation apparatus according to claim 6, further comprising an electrode type detecting control unit for detecting the type of said active electrode, and controlling said target current value selecting unit.

11. An electric surgical operation apparatus according to claim 6, further comprising:
   a feedback electrode which forms a pair with said active electrode;
   a short-circuit impedance detecting unit for detecting an impedance value when said active electrode and said feedback electrode are short-circuited; and
   an electrode nature detecting unit for detecting the type of said active electrode from said impedance value detected by said short-circuit impedance detecting unit.

12. An electric surgical operation apparatus. comprising:
   an active electrode which performs medical treatment to an area to be treated by applying electric energy to said area:
   an electric power supplying unit which supplies electric power to said active electrode:
   a measuring unit which measures at least one of an output voltage value and an output current value supplied to said active electrode from said electric power supplying unit;
   a discerning unit for discerning whether or not the change in at least one of the voltage value and the current value measured by said measuring unit has attained a predetermined change amount; and
   a voltage control unit for controlling said electric power supplying unit so that said supplied electric power is a constant voltage, according to the discerning results discerned by said discerning unit;
   a treating instrument comprising said active electrode and an insulating material having a voltage withstanding value;
   an input unit for inputting the voltage withstanding value of the insulating material of said treating instrument;
   a voltage value correcting unit for correcting the electric power value or the voltage value which does not exceed said voltage withstanding value of said insulating material; and
   a voltage restricting unit for restricting the output voltage of said electric power supplying unit within a range which does not exceed the predetermined voltage value to which correction is made by said voltage value correcting unit.

13. An electric surgical operation apparatus according to claim 12, further comprising:
   a load impedance measuring unit for measuring the load impedance value of said treating instrument which has come into contact with said area to be treated; an insulation destruction judging unit for judging whether or not there has been destruction of insulation of said active electrode, by the state of said load impedance value measured by said load impedance measuring unit; and
   at least one of
      a control unit which controls said electric power supplying unit in order to suppress electric power output of said electric power supplying unit according to the judgment results of said insulation destruction judging unit, and
      a notifying unit for informing the operator of the judgment results of said insulation destruction judging unit.

14. An electric surgical operation apparatus according to claim 13, wherein said insulation destruction judging unit further comprises:
   a stipulated value holding unit for holding a predetermined stipulated value; and
   an insulation destruction judging unit for comparing this held stipulated value with the load impedance measured by said load impedance measuring unit, and passes judgment that the insulation of said treating instrument has been destroyed, in the event that this load impedance is smaller than said stipulated value.

15. An electric surgical operation apparatus, comprising:
   an active electrode, wherein said active electrode is applied to an area of a patient's body to perform one of coagulation and excision;
   a power output selection unit for selecting a power output to said active electrode;
   an electric power supply unit for supplying power to said active electrode;
   a measuring unit that measures at a selected power output at least one of voltage output to said active electrode, current output to said active electrode, and impedance of said area of said patient's body under application by said active electrode; and a voltage control unit for controlling a voltage supplied by said power supply unit;

wherein based on values obtained from said measuring unit, said voltage control unit increases said voltage output to said active electrode until at least one of said voltage output to said active electrode, current output to said active electrode, and impedance of said area of said patient's body under application by said active electrode reaches a first predetermined value, then said voltage control adjusts said voltage output to a second predetermined value and maintains said voltage output at said second predetermined value.

16. An electric surgical operation apparatus according to claim 15, wherein said first predetermined value indicates a condition of said area of said patient's body under application by said active electrode.

17. An electric surgical operation apparatus according to claim 15, further comprising a voltage output selection unit for said second predetermined value.

18. An electric surgical operation apparatus according to claim 15, wherein said voltage control unit includes a gain control unit that is capable of controlling said electric power supply unit to increase and decrease said voltage output.

19. An electric surgical operation apparatus according to claim 15, further comprising a mode selection unit for selecting a mode of operation.

20. An electric surgical operation apparatus according to claim 19, wherein said mode selection unit allows selection of one of an excision mode and a coagulation mode.

* * * * *